US006858005B2

(12) United States Patent
Ohline et al.

(10) Patent No.: US 6,858,005 B2
(45) Date of Patent: Feb. 22, 2005

(54) TENDON-DRIVEN ENDOSCOPE AND METHODS OF INSERTION

(75) Inventors: Robert M. Ohline, Redwood City, CA (US); Joseph M. Tartaglia, Morgan Hill, CA (US); Amir Belson, Cupertino, CA (US); Alex T. Roth, Redwood City, CA (US); Wade A. Keller, San Jose, CA (US); Scott C. Anderson, Sunnyvale, CA (US); Chris A. Julian, Los Gatos, CA (US)

(73) Assignee: Neo Guide Systems, Inc., Los Gatos, CA (US)

( * ) Notice: Subject to any disclaimer, the term of this patent is extended or adjusted under 35 U.S.C. 154(b) by 72 days.

(21) Appl. No.: 10/229,577

(22) Filed: Aug. 27, 2002

(65) Prior Publication Data

US 2003/0045778 A1 Mar. 6, 2003

Related U.S. Application Data

(63) Continuation-in-part of application No. 09/790,204, filed on Feb. 20, 2001, now Pat. No. 6,458,203.
(60) Provisional application No. 60/194,140, filed on Apr. 3, 2000.

(51) Int. Cl.$^7$ .................................................. A61B 1/00
(52) U.S. Cl. ........................ 600/141; 600/146; 600/139
(58) Field of Search ................................. 600/139, 140, 600/141, 142, 143, 145, 146, 147, 148, 149, 150, 151, 152, 101, 102, 103, 109

(56) References Cited

U.S. PATENT DOCUMENTS

| | | | |
|---|---|---|---|
| 2,241,576 A | 5/1941 | Barton |
| 2,767,705 A | 10/1956 | Moore |
| 3,060,972 A | 10/1962 | Sheldon |
| 3,071,161 A | 1/1963 | Ulrich |

(List continued on next page.)

FOREIGN PATENT DOCUMENTS

| | | |
|---|---|---|
| DE | 37 07 787 | 9/1988 |
| JP | 63 136014 | 6/1988 |
| JP | 5-1999 | 1/1993 |
| JP | 111458 | 5/1993 |
| SU | 871-786 | 10/1981 |
| SU | 1256-955 | 9/1986 |
| SU | 1301-701 | 4/1987 |
| WO | WO 02/74235 | 10/2001 |
| WO | WO 03/028547 | 4/2003 |
| WO | WO 03/092476 | 11/2003 |

OTHER PUBLICATIONS

Lee, T.S. et al. (1994). "A Highly Redundant Robot System For Inspection,"*Proceedings of Conference on Intelligent Robots in Factory, Fields, Space and Service*, Houston, TX 1: 142–148.

(List continued on next page.)

*Primary Examiner*—Beverly M. Flanagan
(74) *Attorney, Agent, or Firm*—Wilson Sonsini; Goodrich & Rosati

(57) ABSTRACT

A steerable, tendon-driven endoscope is described herein. The endoscope has an elongated body with a manually or selectively steerable distal portion and an automatically controlled, segmented proximal portion. The steerable distal portion and the segment of the controllable portion are actuated by at least two tendons. As the endoscope is advanced, the user maneuvers the distal portion, and a motion controller actuates tendons in the segmented proximal portion so that the proximal portion assumes the selected curve of the selectively steerable distal portion. By this method the selected curves are propagated along the endoscope body so that the endoscope largely conforms to the pathway selected. When the endoscope is withdrawn proximally, the selected curves can propagate distally along the endoscope body. This allows the endoscope to negotiate tortuous curves along a desired path through or around and between organs within the body.

48 Claims, 17 Drawing Sheets

U.S. PATENT DOCUMENTS

| | | |
|---|---|---|
| 3,190,286 A | 6/1965 | Stokes |
| 3,266,059 A | 8/1966 | Stelle |
| 3,497,083 A | 2/1970 | Anderson et al. |
| 3,546,961 A | 12/1970 | Marton |
| 3,610,231 A | 10/1971 | Takahashi et al. |
| 3,625,084 A | 12/1971 | Low |
| 3,739,770 A | 6/1973 | Mori |
| 3,773,034 A | 11/1973 | Burns et al. |
| 3,897,775 A | 8/1975 | Furihata |
| 3,946,727 A | 3/1976 | Okada et al. |
| 4,054,128 A | 10/1977 | Seufert et al. |
| 4,176,662 A | 12/1979 | Frazer |
| 4,236,509 A | 12/1980 | Takahashi et al. |
| 4,273,111 A | 6/1981 | Tsukaya |
| 4,327,711 A | 5/1982 | Takagi |
| 4,393,728 A | 7/1983 | Larson et al. |
| 4,432,349 A | 2/1984 | Oshiro |
| 4,489,826 A | 12/1984 | Dubson |
| 4,494,417 A | 1/1985 | Larson et al. |
| 4,499,895 A | 2/1985 | Takayama |
| 4,503,842 A | 3/1985 | Takayama |
| 4,543,090 A | 9/1985 | McCoy |
| 4,551,061 A | 11/1985 | Olenick |
| 4,559,928 A | 12/1985 | Takayama |
| 4,566,843 A | 1/1986 | Iwatsuka et al. |
| 4,592,341 A | 6/1986 | Omagari et al. |
| 4,621,618 A | 11/1986 | Omagari |
| 4,646,722 A | 3/1987 | Silverstein et al. |
| 4,651,718 A | 3/1987 | Collins et al. |
| 4,683,773 A | 8/1987 | Diamond |
| 4,686,963 A | 8/1987 | Cohen et al. |
| 4,712,969 A | 12/1987 | Kimura |
| 4,753,222 A | 6/1988 | Morishita |
| 4,753,223 A | 6/1988 | Bremer |
| 4,787,369 A | 11/1988 | Allred, III et al. |
| 4,788,967 A | 12/1988 | Ueda |
| 4,793,326 A | 12/1988 | Shishido |
| 4,799,474 A | 1/1989 | Ueda |
| 4,815,450 A | 3/1989 | Patel |
| 4,832,473 A | 5/1989 | Ueda |
| 4,834,068 A | 5/1989 | Gottesman |
| 4,873,965 A | 10/1989 | Danieli |
| 4,879,991 A | 11/1989 | Ogiu |
| 4,884,557 A | 12/1989 | Takehana et al. |
| 4,890,602 A | 1/1990 | Hake |
| 4,895,431 A | 1/1990 | Tsujiuchi et al. |
| 4,899,731 A | 2/1990 | Takayama et al. |
| 4,904,048 A | 2/1990 | Sogawa et al. |
| 4,930,494 A | 6/1990 | Takehana et al. |
| 4,957,486 A | 9/1990 | Davis |
| 4,971,035 A | 11/1990 | Ito |
| 4,977,887 A | 12/1990 | Gouda |
| 4,987,314 A | 1/1991 | Gotanda et al. |
| 5,005,558 A | 4/1991 | Aomori |
| 5,018,509 A | 5/1991 | Suzuki et al. |
| 5,125,395 A | 6/1992 | Adair |
| 5,159,446 A | 10/1992 | Hibino et al. |
| 5,174,277 A | 12/1992 | Matsumaru |
| 5,243,967 A | 9/1993 | Hibino |
| 5,251,611 A | 10/1993 | Zehel et al. |
| 5,271,381 A * | 12/1993 | Ailinger et al. ............. 600/128 |
| 5,271,382 A | 12/1993 | Chikama |
| 5,297,443 A | 3/1994 | Wentz |
| 5,337,732 A * | 8/1994 | Grundfest et al. .......... 600/116 |
| 5,337,733 A | 8/1994 | Bauerfeind et al. |
| 5,370,108 A | 12/1994 | Miura et al. |
| 5,383,852 A | 1/1995 | Stevens-Wright |
| 5,394,864 A | 3/1995 | Kobayashi et al. |
| 5,400,769 A | 3/1995 | Tanii et al. |
| 5,460,166 A | 10/1995 | Yabe et al. |
| 5,460,168 A | 10/1995 | Masubuchi et al. |
| 5,469,840 A | 11/1995 | Tanii et al. |
| 5,479,930 A | 1/1996 | Gruner et al. |
| 5,482,029 A | 1/1996 | Sekiguchi et al. |
| 5,487,757 A | 1/1996 | Truckai et al. |
| 5,507,717 A | 4/1996 | Kura et al. |
| 5,522,788 A | 6/1996 | Kuzmak |
| 5,531,664 A | 7/1996 | Adachi et al. |
| 5,551,945 A | 9/1996 | Yabe et al. |
| 5,556,370 A | 9/1996 | Maynard |
| 5,558,619 A | 9/1996 | Kami et al. |
| 5,577,992 A | 11/1996 | Chiba et al. |
| 5,624,380 A | 4/1997 | Takayama et al. |
| 5,626,553 A | 5/1997 | Frassica et al. |
| 5,645,520 A | 7/1997 | Nakamura et al. |
| 5,658,238 A | 8/1997 | Suzuki et al. |
| 5,662,587 A | 9/1997 | Grundfest et al. |
| 5,665,050 A | 9/1997 | Benecke |
| 5,667,476 A | 9/1997 | Frassica et al. |
| 5,733,245 A | 3/1998 | Kawano |
| 5,749,828 A | 5/1998 | Solomon et al. |
| 5,752,912 A | 5/1998 | Takahashi et al. |
| 5,759,151 A | 6/1998 | Sturges |
| 5,779,624 A | 7/1998 | Chang |
| 5,810,715 A | 9/1998 | Moriyama |
| 5,810,717 A | 9/1998 | Maeda et al. |
| 5,860,914 A | 1/1999 | Chiba et al. |
| 5,876,373 A | 3/1999 | Giba et al. |
| 5,885,208 A | 3/1999 | Moriyama |
| 5,897,488 A | 4/1999 | Ueda |
| 5,906,591 A | 5/1999 | Dario et al. |
| 5,916,147 A | 6/1999 | Boury |
| 5,921,915 A | 7/1999 | Aznoian et al. |
| 5,941,815 A | 8/1999 | Chang |
| 5,976,074 A | 11/1999 | Moriyama |
| 5,989,182 A | 11/1999 | Hori et al. |
| 5,989,230 A | 11/1999 | Frassica |
| 5,993,381 A | 11/1999 | Ito |
| 6,036,636 A | 3/2000 | Motoki et al. |
| 6,066,132 A | 5/2000 | Chen et al. |
| 6,099,485 A | 8/2000 | Patterson |
| 6,149,581 A | 11/2000 | Klingenstein |
| 6,162,171 A | 12/2000 | Ng et al. |
| 6,174,280 B1 | 1/2001 | Oneda et al. |
| 6,179,776 B1 | 1/2001 | Adams et al. |
| 6,210,337 B1 * | 4/2001 | Dunham et al. ............ 600/462 |
| 6,270,453 B1 * | 8/2001 | Sakai ......................... 600/141 |
| 6,402,687 B1 | 6/2002 | Ouchi |
| 6,408,889 B1 * | 6/2002 | Komachi ..................... 138/120 |
| 6,468,203 B2 | 10/2002 | Belson |
| 6,482,149 B1 * | 11/2002 | Torii .......................... 600/142 |
| 6,610,007 B2 | 8/2003 | Tartaglia et al. |
| 2002/0062062 A1 | 5/2002 | Belson et al. |
| 2002/0062063 A1 | 5/2002 | Ogura et al. |
| 2002/0120178 A1 | 8/2002 | Tartaglia et al. |
| 2002/0161281 A1 | 10/2002 | Jaffe et al. |
| 2003/0083550 A1 * | 5/2003 | Miyagi ....................... 600/141 |

OTHER PUBLICATIONS

Slatkin et al. (1995). "The Development of a Robotic Endocscope,"*Proceedings 1995 IEEE/RSJ International Conference on Human Robot Interaction and Cooperative Robots*, Pittsburg, PA 195(2) pp. 162.171.

Hasson, H.M. (May, 1979). Technique of Open Laparoscopy: Equipment and Technique (from step 1 to step 9), 2424 North Clark Street, Chicago, Illinois 60614, 3 pages.

McKernan. "History: Laparoscopic General Surgery: from 1983 to Apr. 11, 1989," 4 pages.

* cited by examiner

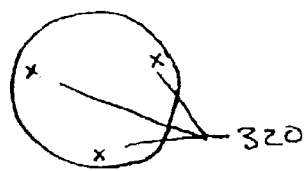
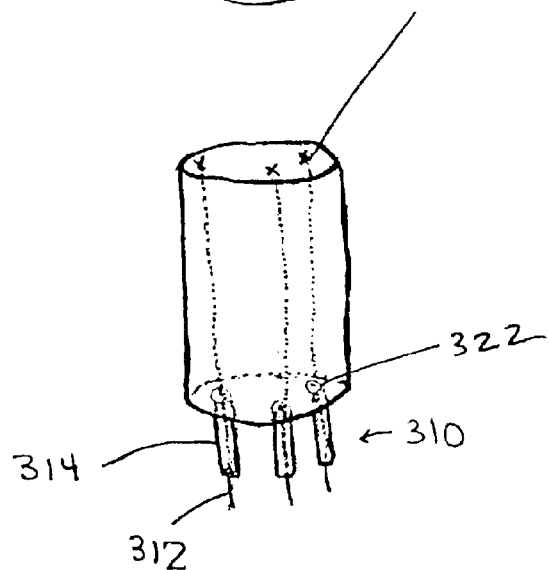
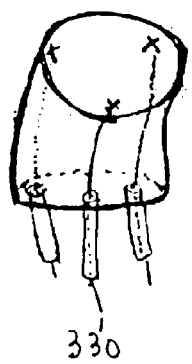
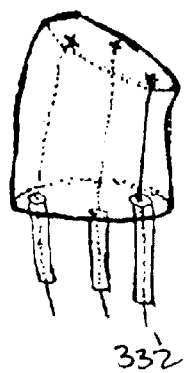
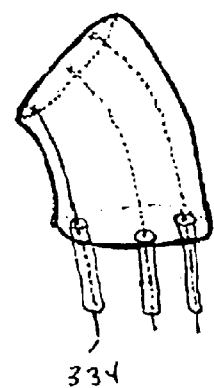
Fig. 3D   Fig. 3E   Fig. 3F

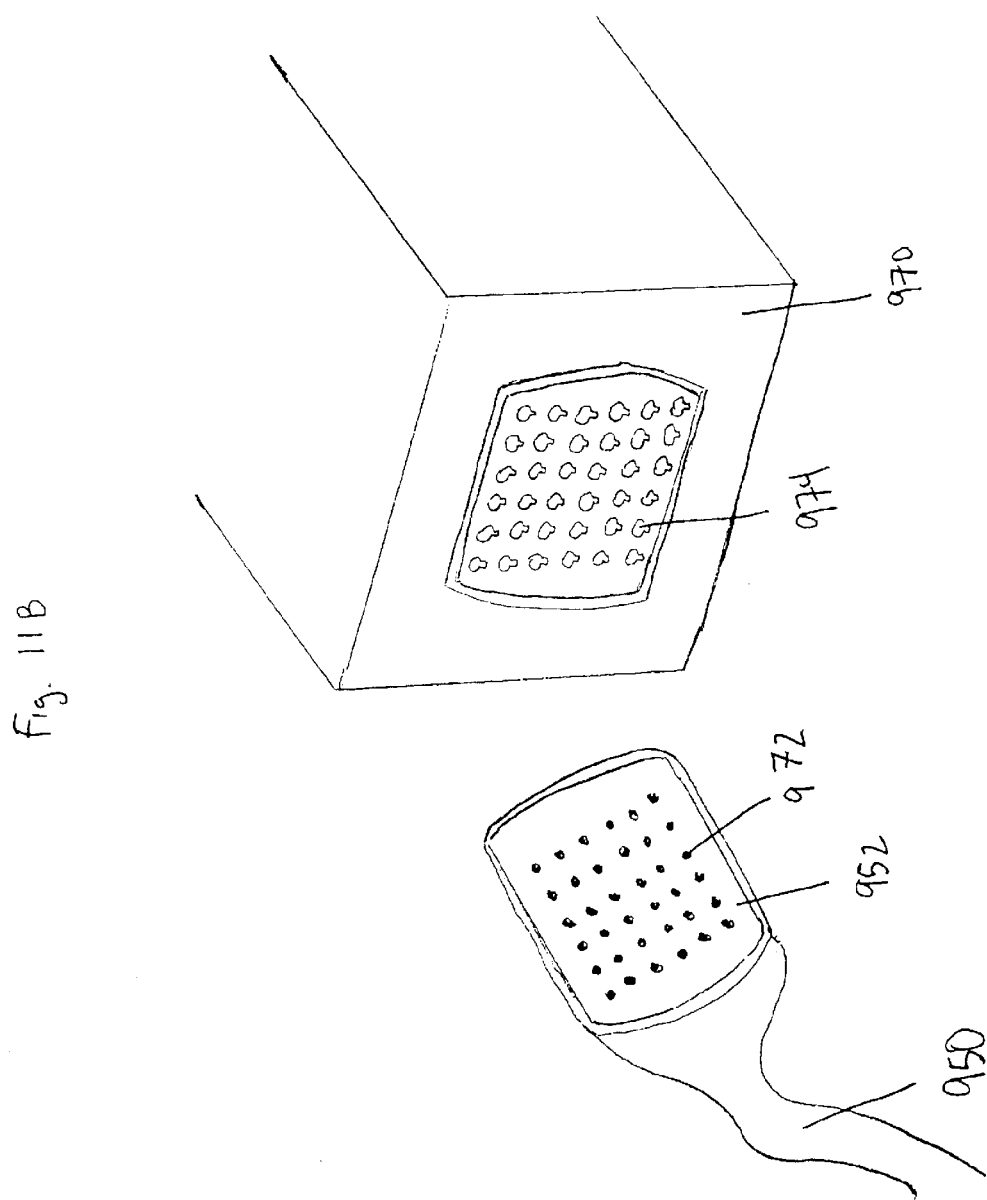

TENDON-DRIVEN ENDOSCOPE AND METHODS OF INSERTION

CROSS-REFERENCE TO RELATED APPLICATIONS

This application is a continuation-in-part of U.S. patent application Ser. No. 09/790,204 entitled "Steerable Endoscope and Improved Method of Insertion" filed Feb. 20, 2001, now U.S. Pat. No. 6,458,203 which claims the benefit of priority to U.S. Provisional Patent Application Serial No. 60/194,140 entitled the same and filed Apr. 3, 2000, both of which are incorporated herein by reference in their entirety.

FIELD OF THE INVENTION

The present invention relates generally to endoscopes and endoscopic procedures. More particularly, it relates to a method and apparatus to facilitate insertion of a flexible endoscope along a tortuous path, such as for colonoscopic examination and treatment.

BACKGROUND OF THE INVENTION

An endoscope is a medical instrument for visualizing the interior of a patient's body. Endoscopes can be used for a variety of different diagnostic and interventional procedures, including colonoscopy, bronchoscopy, thoracoscopy, laparoscopy and video endoscopy.

Colonoscopy is a medical procedure in which a flexible endoscope, or colonoscope, is inserted into a patient's colon for diagnostic examination and/or surgical treatment of the colon. A standard colonoscope is typically 135–185 cm in length and 12–19 mm in diameter, and includes a fiberoptic imaging bundle or a miniature camera located at the instrument's tip, illumination fibers, one or two instrument channels that may also be used for insufflation or irrigation, air and water channels, and vacuum channels. The colonoscope is inserted via the patient's anus and is advanced through the colon, allowing direct visual examination of the colon, the ileocecal valve and portions of the terminal ileum.

Insertion of the colonoscope is complicated by the fact that the colon represents a tortuous and convoluted path. Considerable manipulation of the colonoscope is often necessary to advance the colonoscope through the colon, making the procedure more difficult and time consuming and adding to the potential for complications, such as intestinal perforation. Steerable colonoscopes have been devised to facilitate selection of the correct path though the curves of the colon. However, as the colonoscope is inserted farther into the colon, it becomes more difficult to advance the colonoscope along the selected path. At each turn, the wall of the colon must maintain the curve in the colonoscope. The colonoscope rubs against the mucosal surface of the colon along the outside of each turn. Friction and slack in the colonoscope build up at each turn, making it more and more difficult to advance and withdraw, and can result in looping of the colonoscope. In addition, the force against the wall of the colon increases with the buildup of friction. In cases of extreme tortuosity, it may become impossible to advance the colonoscope all of the way through the colon.

Steerable endoscopes, catheters and insertion devices for medical examination or treatment of internal body structures are described in the following U.S. patents, the disclosures of which are hereby incorporated by reference in their entirety: U.S. Pat. Nos. 4,054,128; 4,543,090; 4,753,223; 4,873,965; 5,174,277; 5,337,732; 5,383,852; 5,487,757; 5,624,380; and 5,662,587.

SUMMARY OF THE INVENTION

The following is a description of steerable endoscopes for the examination of a patient's colon, other internal bodily cavities, or other internal body spaces with minimal impingement upon the walls of those organs. One variation of the steerable endoscope described herein has a segmented, elongated body with a manually or selectively steerable distal portion (at least one segment) and an automatically controlled proximal portion. The selectively steerable distal portion can be flexed in any direction by controlling the tension on tendons, e.g., cables, wires, etc., from their proximal ends; these tendons are routed selectively throughout the length of the endoscope. The controllable proximal portion of the endoscope contains at least one independently articulatable segment that can also be bent in any direction via the tendons, and can be made to assume the shape of the distal segment as the endoscope is advanced distally.

The selectively steerable distal portion can be selectively steered (or bent) up to, e.g., a full 180 degrees, in any direction. A fiberoptic imaging bundle and one or more illumination fibers may extend through the body from the proximal portion to the distal portion. The illumination fibers are preferably in communication with a light source, i.e., conventional light sources, which may be positioned at some external location, or other sources such as LEDs. Alternatively, the endoscope may be configured as a video endoscope with a miniature video camera, such as a CCD camera, positioned at the distal portion of the endoscope body. The video camera may be used in combination with the illumination fibers. Optionally, the body of the endoscope may also include one or two access lumens that may be used, for example, for: insufflation or irrigation, air and water channels, and vacuum channels, etc. Generally, the body of the endoscope is highly flexible so that it is able to bend around small diameter curves without buckling or kinking while maintaining the various channels intact. The endoscope can be made in a variety of sizes and configurations for other medical and industrial applications.

In operation, the steerable distal portion of the endoscope may be first advanced into the patient's rectum via the anus. The endoscope may be simply advanced, either manually or automatically by a motor, until the first curvature is reached. At this point, the user (e.g., a physician or surgeon) can actively control the steerable distal portion to attain an optimal curvature or shape for advancement of the endoscope. The optimal curvature or shape is the path that presents the least amount of contact or interference from the walls of the colon. In one variation, once the desired curvature has been determined, the endoscope may be advanced further into the colon such that the automatically controlled segments of the controllable portion follow the distal portion while transmitting the optimal curvature or shape proximally down the remaining segments of the controllable portion. Thus, as the instrument is advanced, it follows the path that the distal portion has defined. The operation of the controllable segments will be described in further detail below.

Tendons, also called tensioning members, may be used to articulate the controllable segments of the endoscope, including the distal steerable portion. Examples of appropriate tendons are push-pull cables that are flexible but minimally compressible or extensible. In one variation, this tendon is a Bowden cable where an internal cable is typically coaxially surrounded by a housing or sleeve through which the cable is free to move. Bowden cables can be used to apply either tensile or compressive forces in order to articulate the endoscope and can be actuated remotely to deliver forces as desired at locations on the endoscope.

In one variation using Bowden push-pull cables for the tendons, three tendons may be attached at sites equally spaced around the circumference of the controllable endoscope segment. Another variation may alternatively use two tendons, as described further below. The sleeves of the Bowden cables may be affixed at the proximal end of the segment, and the internal cables may be attached to the distal end of the same segment. Applying a tensile or compressive force to one of these internal cables causes the segment to bend in the direction of the cable being pushed or pulled. The bending is continuous and proportional to the displacement of the cable. Thus, a segment can be bent in virtually any direction using tendons by applying tension or compression on one or a combination of tendons attached to the distal end of the segment. Other variations of this invention using Bowden cables may use four or more Bowden cables spaced either equally or in specified positions around the circumference of the segment to be bent depending upon the desired articulation. A further variation may even use two Bowden cables in combination with biasing elements, e.g., springs, elastic elements, pistons, etc., to articulate the segments.

Another variation of the tendon uses a non-compressible, non-extensible push-pull cable in compression rather than in tension in order to bend a segment. Alternatively, a combination of tendons under both compression and tension could also be used.

The controllable proximal portion of the endoscope is comprised of at least one segment and preferably many segments that are each articulatable relative to one another via a controller and/or a computer located at a distance from the endoscope. In one variation, the majority of the insertable length of the endoscope comprises controllable segments. Segments are preferably non-compressible and non-expansible, and therefore maintain a constant length along their centerline when bending. An example describing such a variation may be found in U.S. patent application Ser. No. 09/790,204 entitled "Steerable Endoscope and Improved Method of Insertion", which is commonly owned and incorporated herein by reference in its entirety. Each of the segments may have tendons to allow for controlled motion of the segments in space. Thus, coordinating the articulation of individual tendons can bend each segment across a wide range of motion. Individual tendons can be actuated by, for example, an electromechanical motor operably connected to the proximal end of the tendon. Alternatively, pneumatic or hydraulic cylinders, pneumatic or hydraulic motors, solenoids, shape memory alloy wires, or electronic rotary actuators could be utilized to actuate the segments using the tendons.

Another variation of the endoscope uses ring-shaped support pieces, or vertebrae, as control rings to achieve bendable segments. A segment is comprised of a plurality of adjacent or stacked vertebrae where the vertebrae are connected to each other by jointed sections, e.g., hinged joints, giving the segment flexibility in any direction. Thus, vertebra-type control rings can be hinged to adjacent vertebrae by flanges with through holes. In one variation, pairs of hinge joints project perpendicularly from the face of each vertebra and can connect to the hinge joints of adjacent vertebrae both proximally and distally. Each pair of hinge joints allows limited motion in one axis. The hinge joints projecting from the opposite face of the vertebra are preferably located 90 degrees in rotation from the pair on the other face of the vertebra. This creates a second axis of motion in a plane perpendicular to the first. Adding additional vertebrae in this way result in a segment that could be bent in any direction. For example, approximately ten vertebrae could be linked to create one such segment. Other variations can have more or fewer vertebrae per segment.

In addition to hinged joints, there are other features that could be included in the control ring. Thus, the inner surface of the vertebra could have channels forming a common lumen in the endoscope, such as for the working channels, the air and water channels, the optical fiber channels, tendons, and so forth. The vertebra could also include attachment sites for the tendons, including the sleeve and inner cable of the Bowden cable embodiments. Further, the outer edge of the control ring could include channels for holding tendons that control more distal segments. These channels could provide methods of arranging and organizing such tendons. For example, in another variation, the tendons controlling more distal segments are helically wound around the outer surface of more proximal segments as the tendons project proximally to the controller. Such helical winding could prevent unintended tension on tendons controlling more distal segments when proximal segments are bent. Alternatively, the tendons can include excess "slack." Such excess slack could also help prevent proximal segments from being constrained by bypassing tendons controlling more distal segments.

Another variation of the control ring omits hinged vertebrae, but instead relies on a flexible backbone throughout the endoscope, to which control rings (also called support rings) are attached at intervals. In one variation using a Bowden cable, the tendon inner cables are attached at the most distal control ring in a segment, and the tendon sleeve is attached at the most proximal control ring. The control rings may have spaces allowing components to pass through the segments, and most of the same features described for the vertebra-type control rings.

A proximal handle may be attached to the proximal end of the endoscope and may include imaging devices connected to the fiberoptic imaging bundle for direct viewing and/or for connection to a video camera or a recording device. The handle may be connected to other devices, e.g., illumination sources and one or several luer lock fittings for connection to various instrument channels. The handle may also be connected to a steering control mechanism for controlling the steerable distal portion. The handle may optionally have the steering controller integrated directly into the handle, e.g., in the form of a joystick, conventional disk controller using dials or wheels, etc.

As the endoscope is advanced or withdrawn axially, a depth referencing device, or axial transducer, may be used to measure the relative current depth (axial position) of the endoscope. This axial motion transducer can be made in many possible configurations, such as devices that work by contacting, signaling, or communicating to the endoscope. For example, as the body of the endoscope slides through the transducer, it produces a signal indicating the axial position of the endoscope body with respect to the fixed point of reference. This measure corresponds to the depth of the endoscope within the body cavity. The transducer may also use non-contact methods for measuring the axial position of the endoscope body, such as optical, capacitive, resistive, radio frequency or magnetic detection.

Another variation of the endoscope is fully articulatable over its entire length. Thus, for example, if the endoscope is a standard length of 180 cm, a total of 18 segments (including the steerable distal end), each 10 cm long, could be combined to create a fully articulating, controllable endoscope. In an alternative variation, a passive region proximal to the automatically controlled proximal region could be made of a flexible tubing member that can conform to an infinite variety of shapes.

In this variation, the entire assembly, i.e. segments, tendons, etc., may be encased in a sheath or covering of a biocompatible material, e.g. a polymer, that is also preferably lubricious to allow for minimal friction resistance during endoscope insertion and advancement into a patient. Because the endoscope is used medically, it may be desirable that this covering being removable, replaceable and/or sterilizable.

Similarly, it is desirable that the endoscope be easily disconnected from the controller. The tendons projecting proximally from the segments of the endoscope are collectable in a umbilicus that has an interface which couples with a controller unit containing the actuators, e.g., motors, that apply force to the tendons. This interface may be a quick-disconnect mechanism between the tendons and the controller. One variation of the quick-disconnect mechanism is a "nail head" positionable in a slot design in which the terminus of each tendon cable is configured into, e.g., a flattened protrusion. An array of such tendons at the end of the umbilicus mates with an interface on the controller. The flattened tendon ends may be fitted into corresponding slots defined in the controller housing. The corresponding fit enables the tendon ends to be removably secured within their respective slots and thereby allows the actuators to apply force to specific tendons. Further, the controller can determine the shape of a segment based on the tension being applied by its controlling tendons. The controller can also be adapted to determine segment configuration based upon the position of the cable relative to the cable housing. Moreover, the controller may be further adapted to sense the amount of rotation or linear movement of the controlling tendons and can determine segment configuration based upon this data.

Many alternatives of the quick-disconnect mechanism are contemplated by this invention. Another variation has a mating connector with pins that couple to dimpled receptors; motions of the pins against the receptor are translated into motion of the tendons, e.g. using levers, gears or gear racks, or threaded couplings.

A typical endoscope has a diameter less than 20 mm, although various industrial applications may utilize endoscopes having a diameter greater than 20 mm. Likewise, one variation of this invention also has a radial dimension of less than 20 mm. In another variation of the invention, the radius of more distal segments decreases in a telescope-like fashion. This allows the steerable distal portion to have a much smaller radius, e.g., 12.5 mm, than the more proximal segments. In this variation, the larger radius of more proximal segments provides increased space for tendons from distal segments.

Another alternative variation of this invention uses fewer segments by having segments of different lengths. Thus, more distally located segments can be made shorter, e.g., the most distal segment can have a length of 6 cm, and more proximally located segments increasingly longer, e.g., up to 20 cm length for the most proximal segment. This variation modifies the way selected curves are propagated by the advancement of the endoscope, resulting in an "averaging" or smoothing of the curve as it propagates down the scope. In this variation, a special algorithm can be used to coordinate the automation of the differently sized segments.

One method of propagating the selected turns of the steerable tip along the body of the endoscope involves having the endoscope follow the pathway selected by the user as it is advanced or withdrawn from the body. This method begins by inserting the distal end of the endoscope into a patient, either through a natural orifice or through an incision, and steering the selectively steerable distal portion to select a desired path. When the endoscope body is advanced or inserted further into the patient's body, the electronic controller registers the motion and controls the proximal portion of the endoscope to assume the curve selected by the user when the steerable distal tip was in approximately the same position within the body. Similarly, when the endoscope is withdrawn proximally, the selected curves are propagated distally along the endoscope body, either automatically or passively.

BRIEF DESCRIPTION OF THE DRAWINGS

FIGS. 3B to 3F show the use of three tendons to actuate a controllable segment used in the endoscope of the present invention.

FIG. 11B shows a second variation of a quick-release mechanism for attaching and detaching the tendon driven endoscope from the actuators that relies on a nail-head configuration to actuate the tendons.

DETAILED DESCRIPTION OF THE INVENTION

Figure 1:
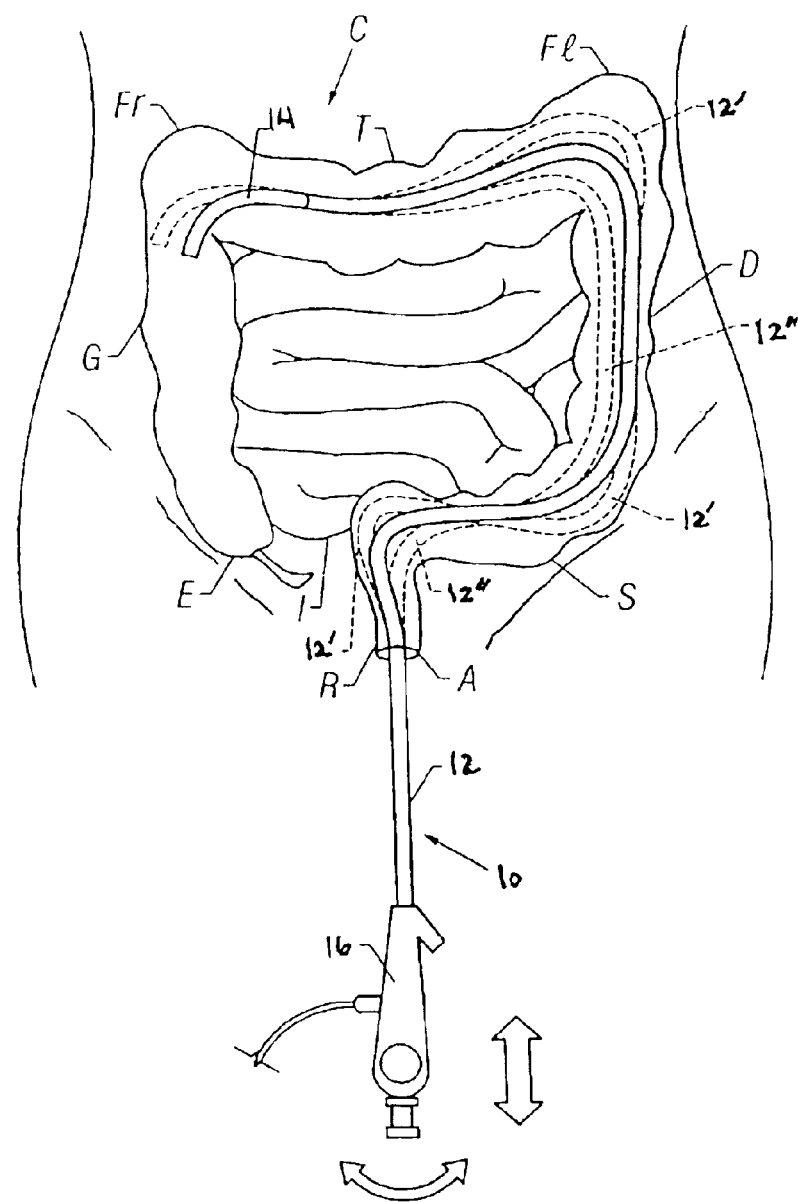
FIG. 1 shows a representation of a conventional endoscope in use.

FIG. 1 shows a prior art colonoscope 10 being employed for a colonoscopic examination of a patient's colon C. The colonoscope 10 has a proximal handle 16 and an elongate body 12 with a steerable distal portion 14. The body 12 of the colonoscope 10 has been lubricated and inserted into the colon C via the patient's anus A. Utilizing the steerable distal portion 14 for guidance, the body 12 of the colonoscope 10 has been maneuvered through several turns in the patient's colon C to the ascending colon G. Typically, this involves a considerable amount of manipulation by pushing, pulling and rotating the colonoscope 10 from the proximal end to advance it through the turns of the colon C. After the steerable distal portion 14 has passed, the walls of the colon C maintains the curve in the flexible body 12 of the colonoscope 10 as it is advanced. Friction develops along the body 12 of the colonoscope 10 as it is inserted, particularly at each turn in the colon C. Because of the friction, when the user attempts to advance the colonoscope 10, the body 12' tends to move outward at each curve, pushing against the wall of the colon C, which exacerbates the problem by increasing the friction and making it more difficult to advance the colonoscope 10. On the other hand, when the colonoscope 10 is withdrawn, the body 12" tends to move inward at each curve taking up the slack that developed when the colonoscope 10 was advanced. When the patient's colon C is extremely tortuous, the distal end of the body 12 becomes unresponsive to the user's manipulations, and eventually it may become impossible to advance the colonoscope 10 any farther. In addition to the difficulty that it presents to the user, tortuosity of the patient's colon also increases the risk of complications, such as intestinal perforation.

Figure 2:
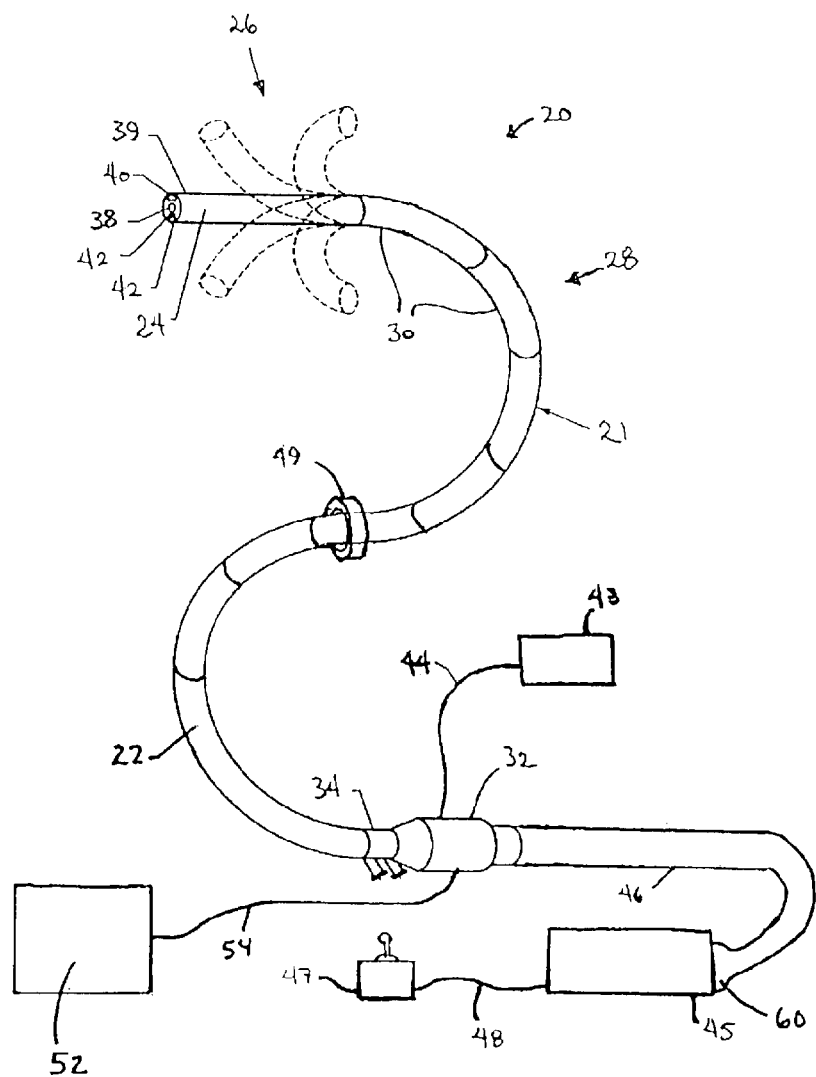
FIG. 2 shows a variation of the tendon driven endoscope of the present invention.

FIG. 2 shows a variation of the tendon driven endoscope 20 of the present invention. The endoscope 20 has an elongate body 21 with a manually or selectively steerable distal portion 24, an automatically controlled portion 28, and a flexible and passively manipulated proximal portion 22, which may be optionally omitted from the device. The steerable distal portion 24 can be articulated by hand or with mechanical assistance from actuators. The automatically controlled portion 28 is segmented, and each segment is capable of bending through a full range of steerable motion. The distal portion 24 is also a controllable segment.

The selectively steerable distal portion 24 can be selectively steered or bent up to, e.g., a full 180° bend in any direction 26, as shown. A fiberoptic imaging bundle 40 and one or more illumination fibers 42 may extend through the body 21 from the proximal portion 22 to the distal portion 24. Alternatively, the endoscope 20 may be configured as a video endoscope with a miniaturized video camera, such as a CCD or CMOS camera, positioned at the distal portion 24 of the endoscope body 21. The images from the video camera can be transmitted to a video monitor by a transmission cable or by wireless transmission where images may be viewed in real-time and/or recorded by a recording device onto analog recording medium, e.g., magnetic tape, or digital recording medium, e.g., compact disc, digital tape, etc. LEDs or other light sources could also be used for illumination at the distal tip of the endoscope.

The body 21 of the endoscope 20 may also include one or more access lumens 38 that may optionally be used for illumination fibers for providing a light source, insufflation or irrigation, air and water channels, and vacuum channels. Generally, the body 21 of the endoscope 20 is highly flexible so that it is able to bend around small diameter curves without buckling or kinking while maintaining the various channels intact. When configured for use as a colonoscope, the body 21 of the endoscope 20 may range typically from 135 to 185 cm in length and about 13–19 mm in diameter. The endoscope 20 can be made in a variety of other sizes and configurations for other medical and industrial applications.

The controllable portion 28 is composed of at least one segment 30, and preferably several segments 30, which are controllable via a computer and/or electronic controller (controller) 45 located at a distance from the endoscope 20. Each of the segments 30 has tendons mechanically connected to actuators to allow for the controlled motion of the segments 30 in space. The actuators driving the tendons may include a variety of different types of mechanisms capable of applying a force to a tendon, e.g., electromechanical motors, pneumatic and hydraulic cylinders, pneumatic and hydraulic motors, solenoids, shape memory alloy wires, electronic rotary actuators or other devices or methods as known in the art. If shape memory alloy wires are used, they are preferably configured into several wire bundles attached at a proximal end of each of the tendons within the controller. Segment articulation may be accomplished by applying energy, e.g., electrical current, heat, etc., to each of the bundles to actuate a linear motion in the wire bundles which in turn actuate the tendon movement. The linear translation of the actuators within the controller may be configured to move over a relatively short distance, e.g., within a few inches or less such as ±1 inch, to accomplish effective articulation depending upon the desired degree of segment movement and articulation.

It is preferable that the length of the insertable portion of the endoscope comprises controllable segments 30, although a passive proximal portion 22 can also be used. This proximal portion 22 is preferably a flexible tubing member that may conform to an infinite variety of shapes, and may be made from a variety of materials such as thermoset and thermoplastic polymers which are used for fabricating the tubing of conventional endoscopes.

Each segment 30 preferably defines at least one lumen running throughout to provide an access channel through which wires, optical fibers, air and/or water channels, various endoscopic tools, or any variety of devices and wires may be routed. A polymeric covering, or sheath, 39 may also extend over the body of the endoscope 21 including the controllable portion 28 and steerable distal portion 24. This sheath 39 can preferably provide a smooth transition between the controllable segments 30, the steerable distal portion 24, and the flexible tubing of proximal portion 22.

A handle 32 may be attached to the proximal end of the endoscope. The handle 32 may include an ocular connected to the fiberoptic imaging bundle 42 for direct viewing. The handle 32 may otherwise have a connector 54 for connection to a video monitor, camera, e.g., a CCD or CMOS camera, or a recording device 52. The handle 32 may be connected to an illumination source 43 by an illumination cable 44 that is connected to or continuous with the illumination fibers 42.

Alternatively, some or all of these connections could be made at the controller 45. Luer lock fittings 34 may be located on the handle 32 and connected to the various instrument channels.

The handle 32 may be connected to a motion controller 45 by way of a controller cable 46. A steering controller 47 may be connected to the motion controller 45 by way of a second cable 48 or it may optionally be connected directly to the handle 32. Alternatively, the handle may have the steering control mechanism integrated directly into the handle, e.g., in the form of a joystick, conventional disk controllers such as dials, pulleys or wheels, etc. The steering controller 47 allows the user to selectively steer or bend the selectively steerable distal portion 24 of the body 21 in the desired direction 26. The steering controller 47 may be a joystick controller as shown, or other steering control mechanism, e.g., dual dials or rotary knobs as in conventional endoscopes, track balls, touchpads, mouse, or sensory gloves. The motion controller 45 controls the movement of the segmented automatically controlled proximal portion 28 of the body 21. This controller 45 may be implemented using a motion control program running on a microcomputer or using an application-specific motion controller. Alternatively, the controller 45 may be implemented using, e.g., a neural network controller.

The actuators applying force to the tendons may be included in the motion controller unit 45, as shown, or may be located separately and connected by a control cable. The tendons controlling the steerable distal portion 24 and the controllable segments 30 extend down the length of the endoscope body 21 and connect to the actuators. FIG. 2 shows a variation in which the tendons pass through the handle 32 and connect directly to the motion controller 45 via a quick-release connector 60. In this variation, the tendons are part of the control cable 46, although they could independently connect to the actuators, so long as the actuators are in communication with the controller 45.

An axial motion transducer (also called a depth referencing device or datum) 49 may be provided for measuring the axial motion, i.e., the depth change, of the endoscope body 21 as it is advanced and withdrawn. The depth referencing device 49 can be made in many possible configurations. For example, the axial motion transducer 49 in FIG. 2 is configured as a ring 49 that may surround the body 21 of the endoscope 20. The axial motion transducer 49 is preferably attached to a fixed point of reference, such as the surgical table or the insertion point for the endoscope 20 on the patient's body. As the body 21 of the endoscope 20 slides through the axial motion transducer 49, it indicates the axial position of the endoscope body 21 with respect to the fixed point of reference and sends a signal to the electronic controller 45 by telemetry or by a cable. The axial motion transducer 49 may use optical, electronic, magnetic, radio frequency or mechanical methods to measure the axial position of the endoscope body 21.

When the endoscope body 21 is advanced or withdrawn, the axial motion transducer 49 detects the change in position and signals the motion controller 45. The controller can use this information to propagate the selected curves proximally or distally along the controllable portion 28 of the endoscope body 21 to keep the endoscope actively following the pathway selected by the user steering the distal portion 24. The axial motion transducer 49 also allows for the incrementing of a current depth within the colon C by the measured change in depth. This allows the endoscope body 21 to be guided through tortuous curves without putting unnecessary force on the wall of the colon C.

A more detailed description on the construction and operation of a variation of the segments may be found in U.S. patent application Ser. No. 09/969,927 entitled "Steerable Segmented Endoscope and Method of Insertion" filed Oct. 2, 2001, which is incorporated by reference in its entirety.

Figure 3A:
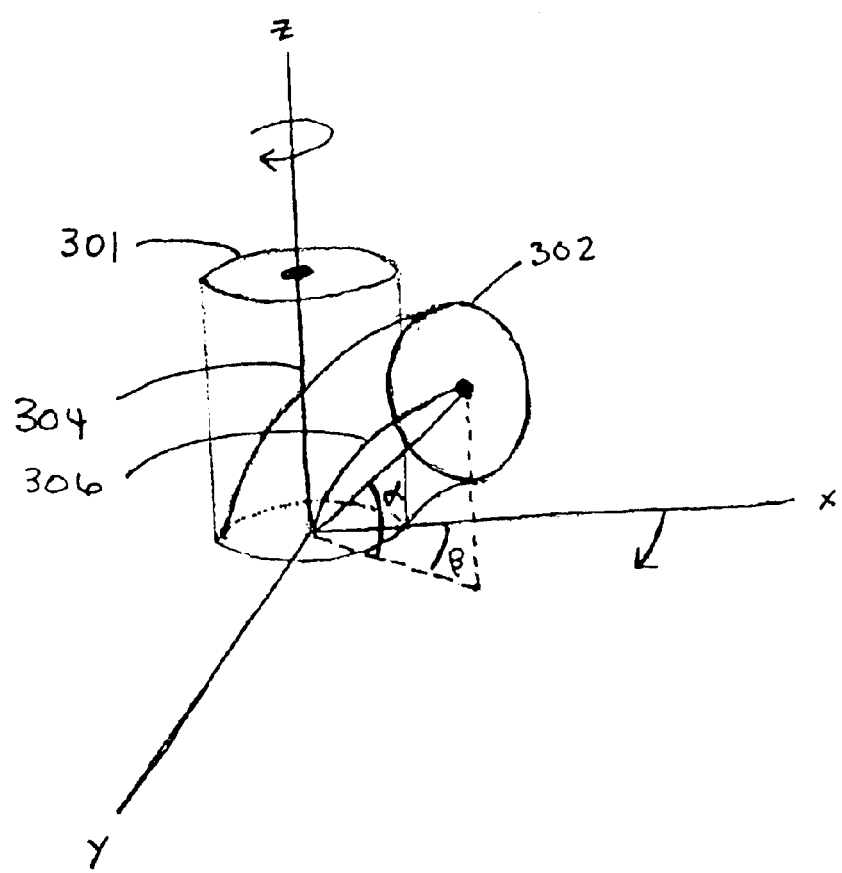
FIG. 3A shows the range of motion of a controllable segment of the present invention actuated by three tendons.

FIG. 3A shows an example of the resulting segment articulation which may be possible through the use of two or three tendons to articulate the controllable segments, including the steerable distal section. FIG. 3A shows one example of a possible range of motion of a controllable segment of the present invention actuated, in this example, by three tendons. A segment in the relaxed, upright position 301 can be bent in virtually any direction relative to the x-y plane. The figure, as an illustrative example, shows a segment 302 that has been bent down and at an angle relative to its original position 301. The angles $\alpha$ and $\beta$ describe the bend assumed by the segment. Angle $\beta$ gives the angle in the x-y plane, while a is the angle describing the motion in the x-z plane. In one variation, the controllable segments of the endoscope can bend through all 360 degrees in the $\beta$ angle and up to 90 degrees in the $\alpha$ angle. An angle a greater than 90 degrees would result in looping of the endoscope. In FIG. 3A, the segment is shown bent approximately 45 degrees along angle $\alpha$. The freedom of movement of a segment is, in part, determined by the articulation method, the size of the segment, the materials from which it is constructed, and the manner in which it is constructed, among others. Some of these factors are discussed herein.

The steerable distal portion, as well as the endoscope and the controllable segments are bendable but preferably not compressible or expansible. Thus, in FIG. 3A, the centerline 304 of the relaxed segment 301 is approximately the same length as the centerline 306 of the segment after bending 302.

FIGS. 3B to 3F show the use of three tendons to actuate a controllable segment used in an endoscope of the present invention. The tendons shown in this example are all Bowden type cables 310 that have an internal cable 312 coaxially surrounded by a housing or sleeve 314 in which the cable is free to move. Bowden cables can be used to apply either tensile or compressive forces, i.e., they may be pushed or pulled, to articulate the endoscope and can be actuated remotely to deliver forces as desired at locations along the endoscope. Force from a tendon is exerted across or through the segment by attaching the tendon cable at the distal end of the segment 320 and the tendon housing 314 at the proximal end of the segment 322. FIG. 3B shows a view of the top of the segment with three attachment sites for the tendon cables indicated 320.

In one variation, three tendons are used to actuate each segment, including the steerable distal portion, although four or more tendons could be used. Three tendons can reliably articulate a segment in any direction without having to rotate the segment or endoscope about its longitudinal axis. The three cable tendons 312 are preferably attached at the distal end of the segment 320 close to the segment's edge, spaced equally apart. In FIG. 3B, tendons are attached at the two o'clock, six o'clock and 10 o'clock positions. It is desirable to use fewer tendons, because of space concerns, since the tendons controlling each segment project proximally to the actuators. Thus, two tendons could be used to control a segment. It may also be desirable to include one or more biasing element, e.g., a spring, to assist in articulating a segment in three dimensions. In another variation, two tendons may be used to articulate a segment in three dimensional space by controlling motion in two directions while rotating the segment about its longitudinal axis.

FIG. 3C shows a relaxed segment with three tendons attached. The tendon sleeves 314 are shown attached to the proximal end of the segment 322 directly below the corresponding cable attachment sites. FIGS. 3D to 3F show this segment bent by each of the controlling tendons 310 separately.

As shown in FIG. 3D, applying tension by pulling on the first tendon 330 results in a bending in the direction of the first tendon 330. That is, looking down on the top of the unbent segment (as in FIG. 3B), if the first tendon is attached at the six o'clock position, then pulling on just this tendon results in bending the segment towards the six o'clock position. Likewise, in FIG. 3E, putting tension only on a second tendon 332 attached at the two o'clock position results in bending the segment towards the two o'clock direction. Finally, pulling on the tendon in the ten o'clock position 334 bends the segment towards the ten o'clock direction. In all cases, the bending is continuous; the greater the tension applied, the further the bending (the $\alpha$ angle, in the x-z plane of FIG. 3A). A segment can be bent in any direction by pulling on individual tendons or a combination of two tendons. Thus, to bend the segment in the twelve o'clock direction, both the second 332 and the third 334 tendon could be pulled with equal force. Alternatively, first tendon 330 in the six o'clock position may be pushed either alone or in combination with second 332 and third tendons 334 being pulled to result in the same configuration.

Figure 4A:
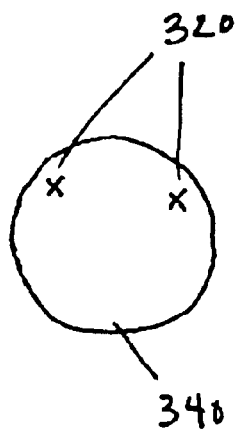
FIGS. 4A and 4B show the use of two tendons to actuate a controllable segment in the endoscope of the present invention.
Figure 4B:
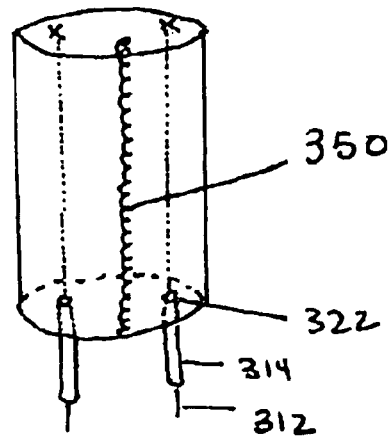

FIGS. 4A and 4B show a variation in which a segment is articulated by two tendons and one biasing element. FIG. 4A shows a planar top view of the segment. The attachment sites for the biasing element 340 and the two tendons 320 are spaced around the perimeter of the distal end of the segment as shown. The tendons 320 may be attached at the two o'clock and ten o'clock positions, looking down on the top of the section, and the biasing element 340 is attached at the six o'clock position. FIG. 4B shows a perspective view of the segment in the unbent configuration. In this variation, the biasing element is configured to apply tension to the side of the segment such that it will bend towards the six o'clock position. The biasing element can be any element that can apply compressive or tensile forces across the segment, e.g. a spring, elastic element, a piston, etc. The segment is held in the neutral or unbent position shown in FIG. 4B by applying tension from both tendons 312. Controlling the amount of tension applied by the tendons results in bending of the segment in three dimensional space. More than one biasing element could also be used with two or more tendons. For example, a biasing element could be located opposite each tendon.

Alternatively, if the tendon is a push-pull cable, and each tendon can apply compression as well as tension, then two tendons can control the motion of segment without any biasing element at all.

Figure 4C:
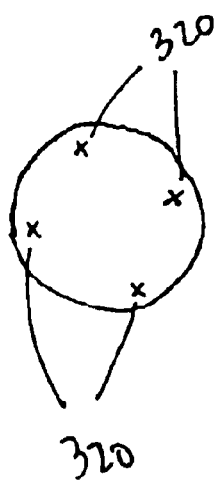
FIGS. 4C and 4D show the use of four tendons to actuate a controllable segment in the endoscope of the present invention.
Figure 4D:
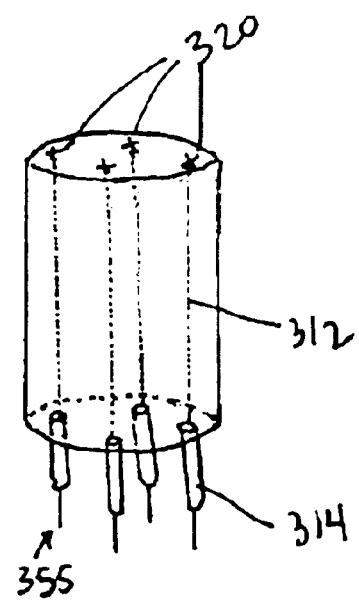

More than three tendons can also be used to control the bending of a segment. FIG. 4C shows a top planar view of a segment that is controlled by four tendons attached in the eleven o'clock, two o'clock, five o'clock and eight o'clock positions. As with the three-tendon embodiment, tension applied on one or a combination of the tendons results in shortening the side of the segment. Thus, if tension is applied only on the tendon attached distally at the eleven o'clock position 355, the corresponding side of the tendon will shorten, and the segment will bend in the eleven o'clock direction.

In all these variations, the circumferential locations of the tendons and/or biasing elements are illustrative and are not intended to be limited to the examples described herein. Rather, they may be varied according to the desired effects as understood by one of skill in the art.

Figure 5:
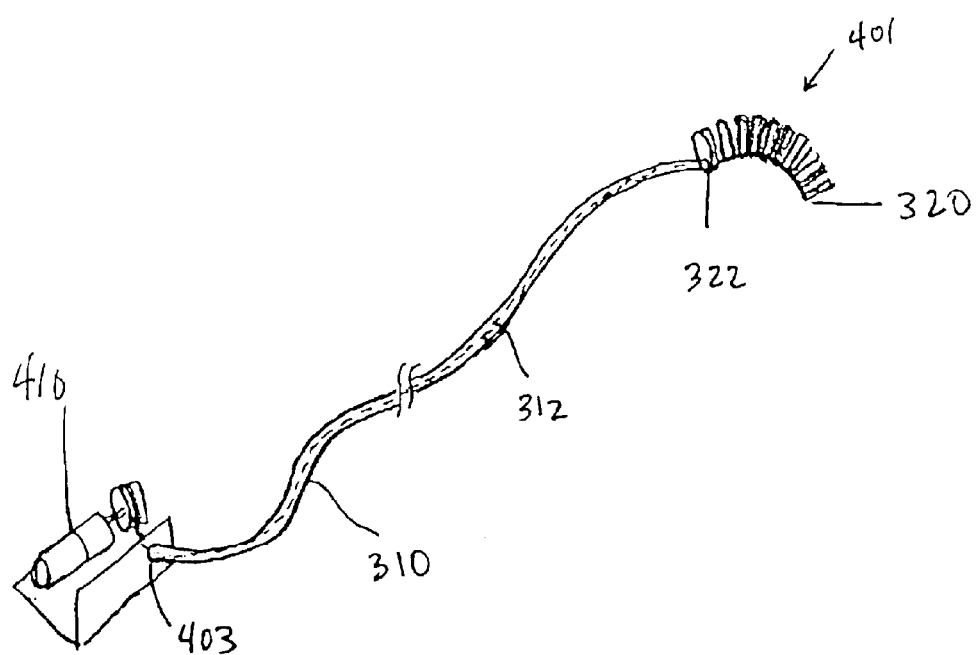
FIG. 5 shows a partial schematic representation of a single tendon bending a segment.

FIG. 5 shows a partial schematic representation of a single tendon bending a segment. For clarity, the other parts of a complete endoscope, including other tendons and segments, have been omitted from FIG. 5. Tension applied to a tendon cable is transferred across the entire segment, resulting in bending. By using a Bowden cable 310 whose sleeve 314 is attached to the base 322 of the segment and also fixed at the proximal actuator end 403, only the intended segment 401 is bent by applying tension to the tendon 312, and more proximal segments are unaffected. The tendon is placed in tension by the actuator 410, which is shown, in this variation, as a motor pulling on the tendon cable 312.

Figure 6A:
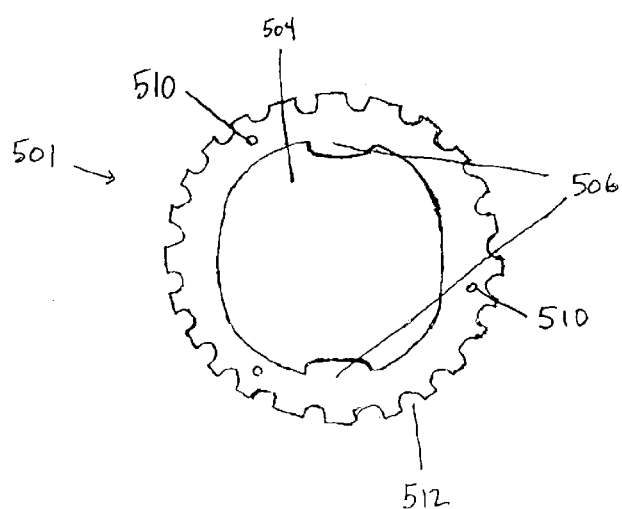
FIGS. 6A and 6B show an end view and a side view, respectively, of a vertebra-type control ring which may be used to form the controllable segments of the endoscope of the present invention.

Linked control rings may provide the flexible structure needed to construct the steerable distal portion and the controllable segments. Two examples of the types of control rings that may be utilized are shown. The first is shown in FIG. 6A which shows a vertebra-type control ring that forms the controllable segments of the present invention. FIG. 6A shows an end view of a single vertebra. Each ring-shaped vertebra 501 can define a central channel or aperture 504 or apertures that can collectively form the internal lumen of the device as previously described. The vertebrae may have two pairs of hinges; the first pair 506 projecting perpendicularly from a first face of the vertebra and a second pair 508, located 90 degrees around the circumference from the first pair, projecting perpendicularly away from the face of the vertebra on a second face of the vertebra opposite to the first face. The hinges shown in FIGS. 6A and 6B are tab-shaped, however other shapes may also be used.

The vertebra control ring in FIG. 6A is shown with three holes 510 through the edge of the vertebra that may act, e.g., as attachment sites for the tendon cable 312 if the vertebra is the most distal vertebra in a segment, or as a throughway for a tendon cable that can actuate the segment in which the vertebra is used. These holes 510 can also be used to attach the sleeve of the Bowden-type tendon cable 314 when the vertebra is the most proximal control disk in a segment. Alternatively, rather than a hole 510, the attachment sites could be a recess or other specialized shape. Although FIG. 6A shows three holes 510, the number of holes may depend upon the number of tendons used to control the segment to which the vertebra belongs. Since the holes 510 may be used as attachment sites for the tendons, there are as many holes as there are tendons controlling the segment.

The outer edge of the vertebra in FIG. 6A may be scalloped to provide spaces 512 for tendon housings of tendons that control more distal segments and bypass the vertebra. These tendon bypass spaces preferably conform to the outer diameter of the tendons used. The number of tendon bypass spaces 512 may vary depending on the number of tendons. Also, the orientation of the tendon bypass spaces may be varied if it is desirable to vary the way in which the bypassing tendons are wound around the endoscope. For example, the spaces 512' in FIG. 6C are oriented at an angle relative to the longitudinal axis of the vertebra, allowing the tendons to wind around the body of the endoscope as they project proximally. Furthermore, the tendon bypass spaces could be lubricated or composed of a lubricious material in order to facilitate free movement of the bypassing tendons across the segment, and prevent interference between the bending of the segment and the bypassing tendons.

Figure 6B:
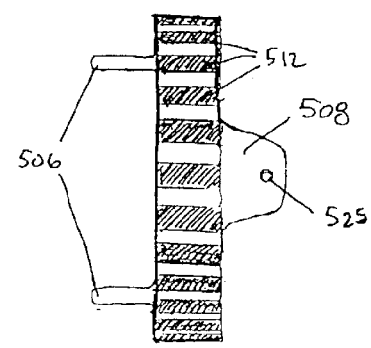
Figure 6C:
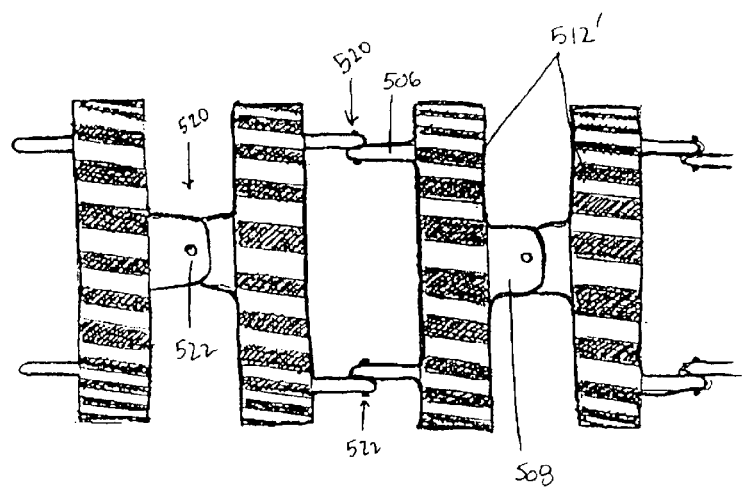
FIG. 6C shows a side view of interconnected vertebra-type control rings used to form the controllable segments of the endoscope of the present invention.

FIGS. 6B and 6C show side views of the same vertebra as FIG. 6A. The two pairs of hinge joints 508, 506 are shown.

Hinge joints 508, 506 are preferably located 90 degrees apart and extend axially so that the hinge joints can pivotally mate with hinge joints from adjacent vertebrae. This mating 520 with adjacent vertebrae is more clearly seen in FIG. 6C. These hinges can be joined, pinned, or connected through the holes 525 as shown 522. Alternatively, hinges may also be made from materials utilizing, e.g., thermoplastics, shape memory alloys, etc. Once hinged, each vertebra can rotate relative to an adjoining vertebra in one axis. However, because vertebrae are hinged to each other in directions alternating by 90 degrees, an assembly of multiple vertebrae is able to move in virtually any direction. The greater the number of vertebrae joined in this manner, the greater the range of motion. In one embodiment, two to ten vertebrae are used to comprise one segment, achieving a length of around 4 cm to 10 cm per segment. The dimensions of both the vertebrae and the hinge joints can be varied, e.g., longer hinge joints will have a greater bending radius when joined to another vertebra. Furthermore, the number of vertebrae per segment can vary, e.g. more than ten vertebrae could be used.

Figure 6D:
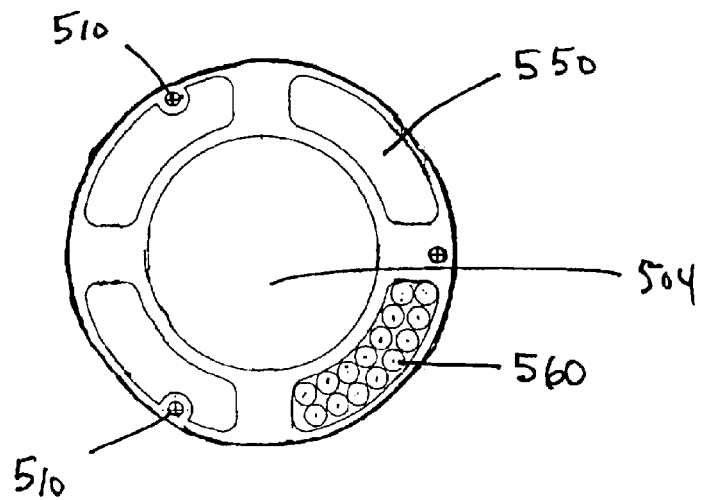
FIGS. 6D and 6E show a side view and a perspective view, respectively, of another embodiment of a vertebra-type control ring.
Figure 6E:
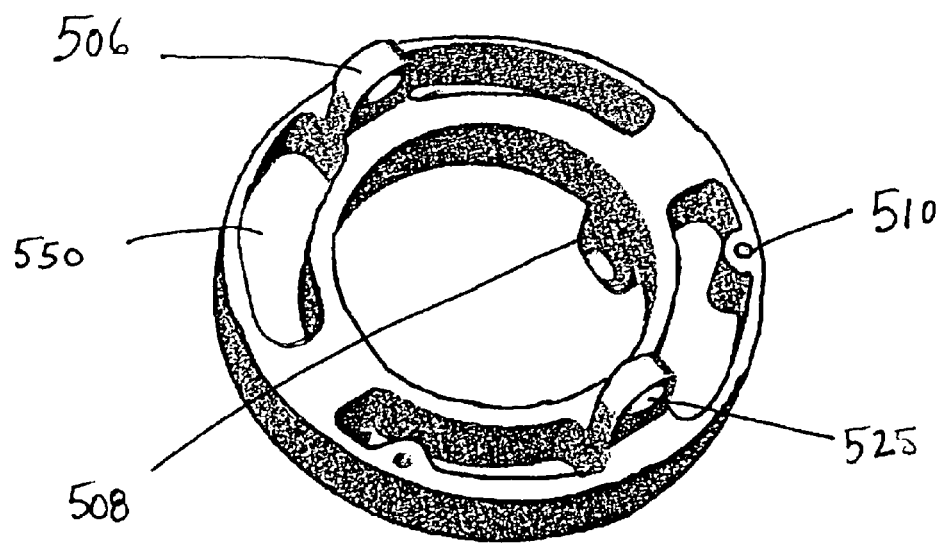

FIGS. 6D and 6E show another variation of a vertebra in sectional and perspective views, respectively. In FIGS. 6D and 6E, the tendons that bypass the segment may be contained within the body of the vertebra in a tendon bypassing space 550 rather than along the outer edge of the vertebra as shown in FIG. 6A. The vertebra of FIGS. 6D and 6E show four tendon bypassing spaces 550, and each space can hold approximately fifteen bypassing tendon sleeves. The number, shape and sizes of the tendon bypassing spaces can be varied. For example, a vertebra could have two tendon bypassing spaces that could hold more than thirty-five tendon sleeves. Moreover, the tendon bypassing space could also be located on the inside of the central aperture or lumen of the vertebra 504.

Although FIG. 6D shows tendon sleeves holding only a single tendon cable 560, more than one tendon cable could be contained in a tendon housing or sleeve. For example, if three tendons articulate a segment, all three tendons could be contained in a single tendon housing. Such a combined tendon housing could further utilize lubrication to accommodate independent movement by individual tendon cables and/or could be divided into compartments that isolate the tendons within the housing.

FIG. 6E also shows a perspective view of the hinge joints 506, 508 that can pivotally mate with pairs of hinge joints from adjacent vertebrae. Although FIGS. 6A and 6B shows two pairs of hinge joints projecting axially, a single hinge joint on each face of the vertebra could also be used. Moreover, as long as the hinge joints can pivotally mate with adjacent vertebrae, the hinge joints can be located at different radial locations from the center of the vertebra. For example, the pairs of hinge joints shown in FIGS. 6A to 6C are located closer to the center of the vertebra than the hinge joints in FIGS. 6D and 6E.

Figure 7A:
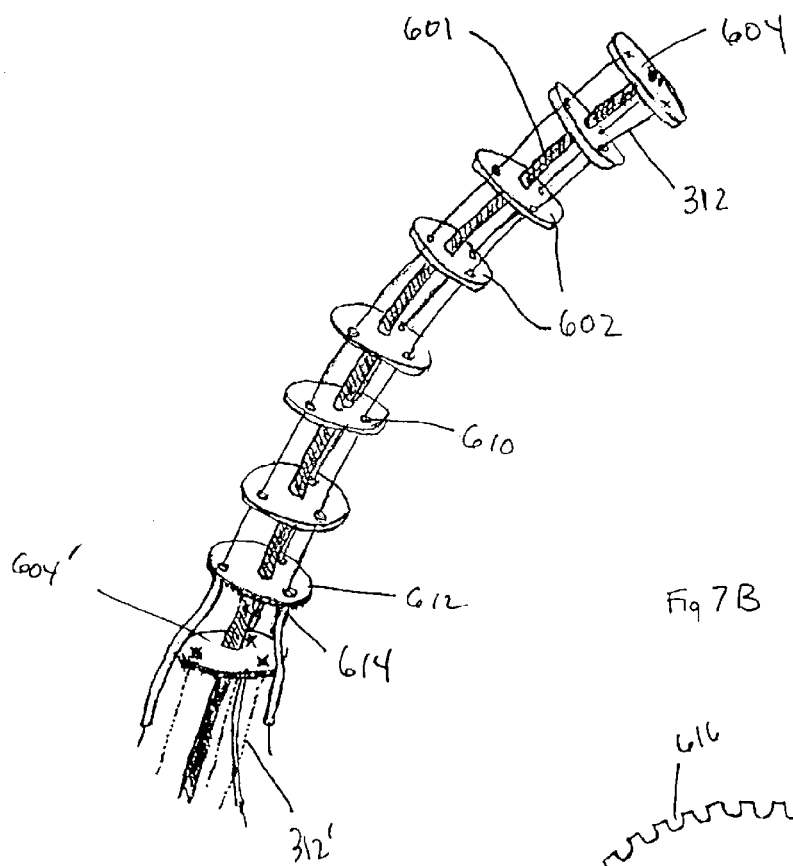
FIG. 7A shows a perspective view of an endoscope device variation with the outer layers removed to reveal the control rings and backbone.

FIG. 7 shows a second variation of control ring. The variation shown in the figure utilizes a flexible backbone 601 preferably made of a material that is relatively non-compressible and non-extensible, to which control rings 602 are attached at intervals. This structure allows bending in a continuous curve in any desired direction. FIG. 7A shows a side view of one controllable segment of this variation with the outer layers removed to show the control rings and backbone. Multiple control rings 602 may be attached to the flexible backbone at regular intervals. Fewer or more control rings could be used to comprise a single segment depending upon the desired degree of articulation. The tendon cable 312 attaches to the most distal control ring of the segment 604. As with the vertebra-type variation, this central backbone embodiment is shown actuated by three tendons 310 attached at sites equally spaced around the edge of the most distal control ring of the segment 604. The tendon cables controlling the segment 312 pass through spaces or holes 610 defined in the control rings 602 through which they are free to move. These holes 610 could be lubricated, lined with a lubricious material or the control rings 602 may be composed of some lubricious material to facilitate cable motion through the holes 610. The tendon sleeve preferably attaches at a location 614 to the most proximal control ring in the segment 612. When a tendon 312 is placed under tension, this force is distributed along the entire segment. Because the inner tendon cable 312 is freely slidable within the tendon sleeve 314, and the tendon sleeve is fixed at both ends of the tendon 614, pulling on the tendon cable causes bending only in the selected segment.

Figure 7B:
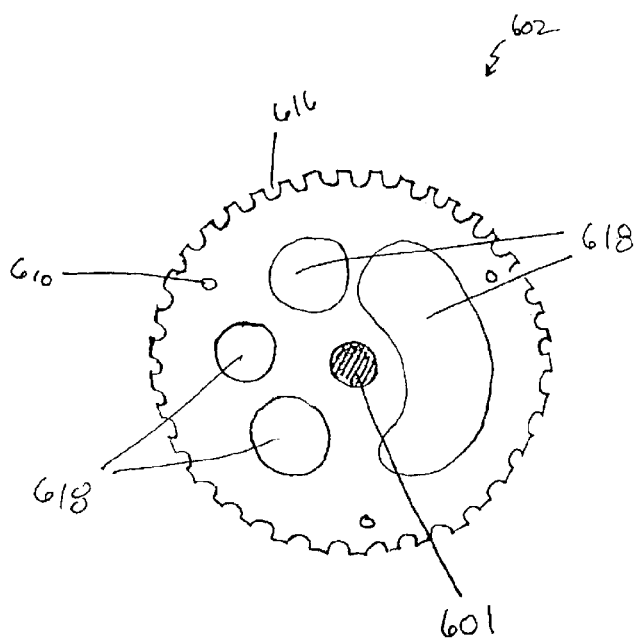
FIG. 7B shows an end view of a variation of the control ring for an endoscope of the present invention.

FIG. 7A also shows the first control ring of a more proximal segment 604'. The tendons controlling the more distal segment may pass over the outside of the more proximal segments as they project proximally to the actuators. The outer edge of the control rings for the flexible backbone embodiment are shown with channels or tendon bypassing spaces 616 for bypassing tendons, as seen in FIG. 7B. As with the vertebra-type control rings, these tendon bypassing spaces could also be located within the control ring, for example, in an enclosed tendon bypassing space.

FIG. 7B shows an end view of control ring 602 which may be used with the flexible backbone embodiment of the endoscope. The center of the control ring contains a channel through which the flexible backbone 601 can be attached. A number of additional channels through the control ring 618 are also shown. These channels can be aligned with channels in neighboring control rings to form an internal lumen or channel for a fiber optic imaging bundle, illumination fibers, etc. as discussed above. Moreover, adjacent control rings may be spaced adjacently to one another at uniform or various distances depending upon the desired degree of bending or control. FIG. 7B shows three equally spaced holes 610 through which the tendon cable can pass; these holes 610 could also be used as attachment sites for the tendon cable, e.g., when the control ring is the most distal control ring in the segment 604, or for the tendon cable sleeve, e.g. when the control ring is the most proximal control ring in the segment 612. These holes 610 could be shaped specifically to receive either the tendon end or the tendon sleeve. Control rings of other designs could be used for different regions of the segment, or for different segments.

Figure 8A:
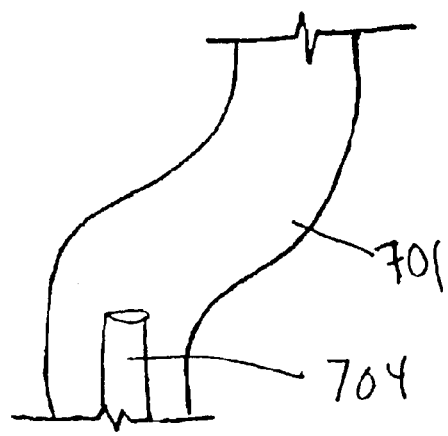
FIGS. 8A to 8C illustrate advancing the tendon driven endoscope of the present invention through a tortuous path.
Figure 8B:
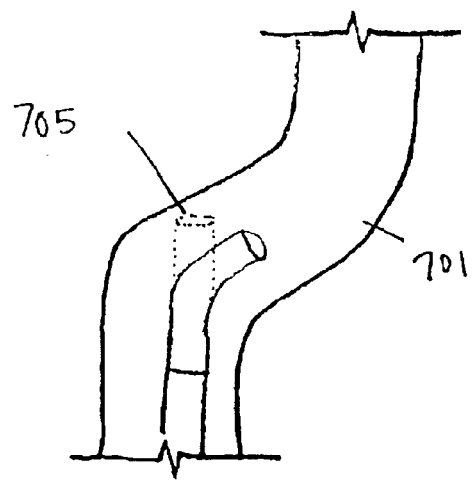
Figure 8C:
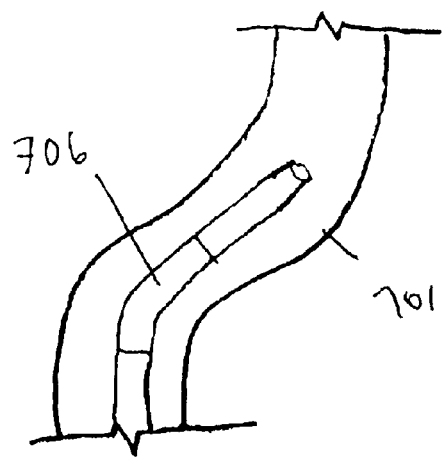

FIGS. 8A to 8C illustrate a variation of the tendon driven endoscope navigating a tortuous path. The path 701 is shown in FIG. 8A. This pathway may represent a portion of colon, for example. In FIG. 8A, the distal tip of the device 704 approaches the designated bend. FIG. 8B shows the distal tip being steered 705 to assume the appropriate curve. This steering could be performed manually by the user, e.g. a doctor, or automatically using an automatic detection method that could determine the proximity of the walls of the pathway. As described, the bending of the steerable tip is performed by placing tension on the tendon, or combination of tendons that results in the appropriate bending.

The device is then advanced again in FIG. 8C; as it is advanced, the selected curve is propagated down the proximal length of the endoscope, so that the bend of the endoscope remains in relatively the same position with respect to the pathway 701. This prevents excessive contact with the walls, and allows the endoscope to move more easily along the tortuous pathway 701. The endoscope is in continuous communication with the motion controller, and the motion controller can monitor the location of the endoscope within the pathway, e.g., depth of insertion, as well as the selected bends or curves that define the pathway of the endoscope. Depth can be determined by, e.g., the axial motion transducer 49 previously described, or by more direct measurement techniques. Likewise, the shape of each segment could be determined by the tension applied to the tendons, or by direct measurement, such as direct measurement of displacement of the tendon cables. The motion controller can propagate the selected shape of a segment at a specified location, or depth, within the body, e.g., by setting the lengths of the sides of more proximal segments equal to the corresponding lengths of the sides of more distal segments as the device is moved distally. The controller can also use this information to automatically steer the body of the endoscope, or for other purposes, e.g. creating a virtual map of the endoscope pathway for analytic use.

In addition to measuring tendon displacement, the motion controller can also adjust for tendon stretch or compression. For example, the motion controller can control the "slack" in the tendons, particularly in tendons that are not actively under tension or compression. Allowing slack in inactive tendons reduces the amount of force that is required to articulate more proximal segments. In one variation, the umbilicus at the distal end of the endoscope may contain space to allow slack in individual tendons.

The bending and advancing process can be done in a stepwise or continuous manner. If stepwise, e.g., as the tendon is advanced by a segment length, the next proximal segment 706 is bent to the same shape as the previous segment or distal steerable portion. A more continuous process could also result by bending the segment incrementally as the tendon is advanced. This could be accomplished by the computer control, for example when the segments are smaller than the navigated curve.

Figure 9:
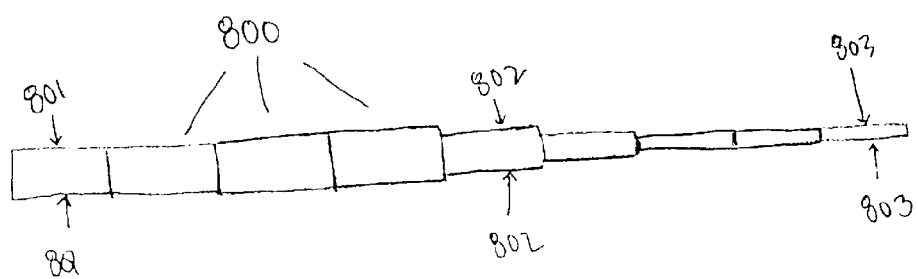
FIG. 9 shows a variation of the tendon driven endoscope of the present invention that has segments of differing diameters.
Figure 10:
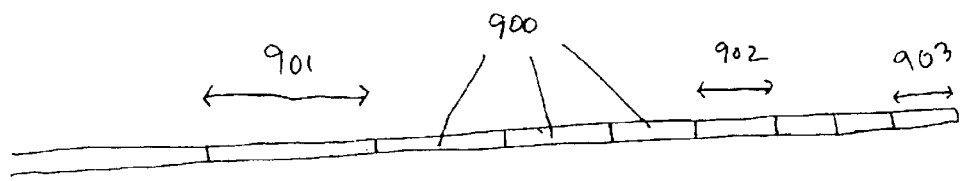
FIG. 10 shows a variation of the tendon-driven endoscope of the present invention that has segments of different length.

Controllable segments, including the steerable distal portion, can be selected to have different dimensions, e.g., different diameters or lengths, even within the same endoscope. Segments of different dimensions may be desirable because of considerations of space, flexibility and method of bending. For example, the more segments in an endoscope, the further it can be steered within a body cavity; however, more segments require more tendons to control the segments. FIGS. 9 and 10 illustrate two variations on tendon driven endoscopes.

FIG. 9 shows a tendon driven endoscope variation that has segments 800 of differing diameters. More distal segments may have a smaller diameter 803 than more proximal segments, e.g., 802, 801. The diameter of a typical endoscope could decrease from, e.g., 20 mm, down to, e.g., 12.5 mm. The endoscope shown in FIG. 9 appears telescoped, as the diameter decreases distally in a stepwise manner. This design would be responsive, e.g., to internal body structures that become increasingly narrow. This design would also help accommodate bypassing tendons from more distal segments as they proceed towards the proximal actuators because of the larger diameter of the more proximal segments. FIG. 9 shows four differently sized segments; however, virtually any number of differently sized segments could be used. Moreover, although the segments appear stepped in this variation, the outer surface may be gently tapered to present a smooth outer surface decreasing in diameter towards the distal end.

FIG. 10 shows another variation of the tendon driven endoscope that has segments of different lengths. Using segments of different lengths may require fewer overall segments 900 to construct an equivalent length of articulatable endoscope. As shown in FIG. 10, more proximal segments 901 are increasingly longer than more distal, e.g., 902, 903, segments. For example, segment length could be decreased from 20 cm at a proximal segment down to 6 cm at a distal most segment. The lengths may be decreased incrementally segment to segment by a constant factor; alternatively, lengths may be decreased geometrically, exponentially, or arbitrarily depending upon the desired articulation. In practice this results in an "averaging" of curves by more distal segments as bends and turns are propagated proximally. In order to accomplish this, the motion controller may be configured to accommodate the differently sized segments accordingly. Alternatively, endoscopes could be comprised of a combination of segments of different length and thickness, depending upon the application.

The tendons that articulate the segments are in mechanical communication with the actuators. However, it may be desirable to have the insertable distal portion of the endoscope be removable from the actuators and controller, e.g., for cleaning or disinfecting. A quick-release mechanism between the proximal end of the endoscope and the actuators is an efficient way to achieve an endoscope that is easily removable, replaceable or interchangeable. For example, the proximal ends of the tendons can be organized to allow predictable attachment to corresponding actuators. The tendons may be organized into a bundle, array, or rack. This organization could also provide other advantages to the endoscope, such as allowing active or passive control of the tendon slack. Furthermore, the proximal ends of each tendon can be modified to allow attachment and manipulation, e.g., the ends of the tendons may be held in a specially configured sheath or casing.

Figure 11A:
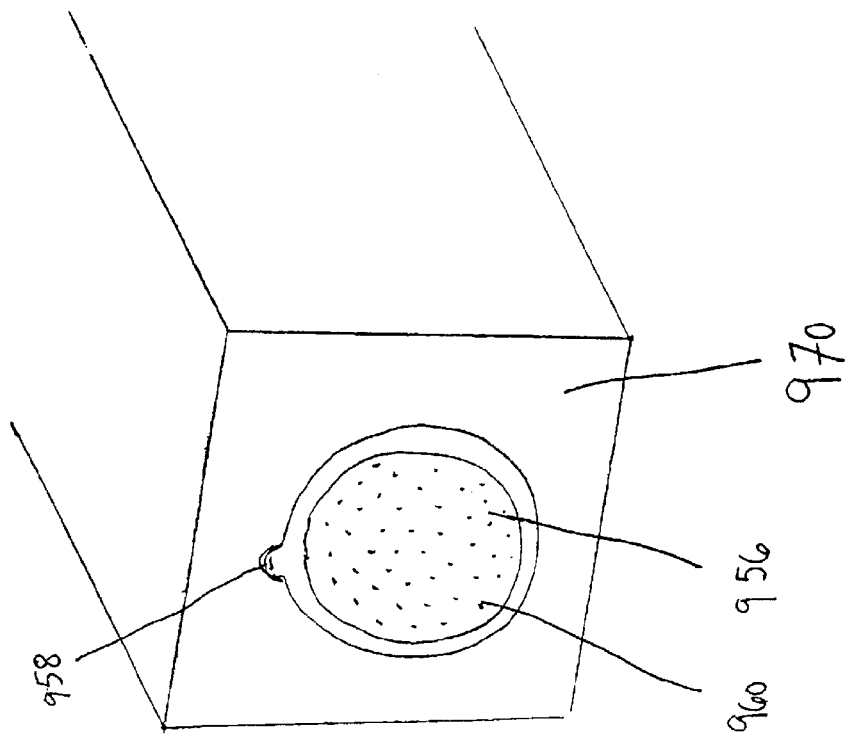
FIG. 11A shows a variation of a quick-release mechanism for attaching and detaching the tendon driven endoscope from the actuators that relies on pins to actuate the tendons.
Figure 11A:
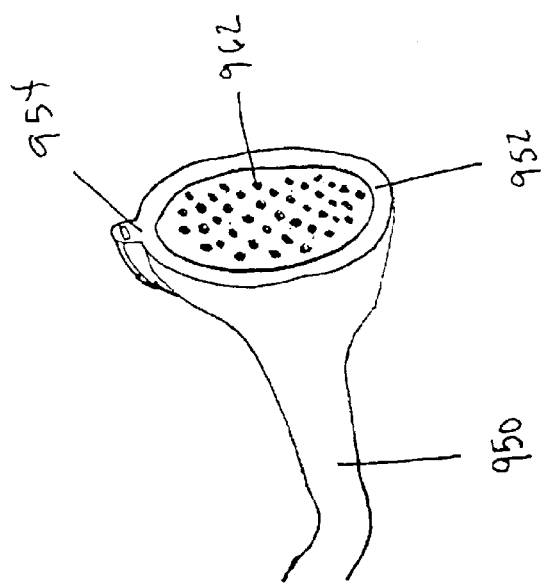

FIGS. 11A and 11B show two variations on quick-release mechanisms for attaching and detaching the tendon driven endoscope from the actuators. FIG. 11A shows one variation of this quick-release mechanism. The proximal end of the tendons is bundled in an umbilicus 950, and the individual tendons terminate in dimpled connectors 962 that are held in an organized array in a connector interface 952. The connector interface 952 mates to a complementary receiving interface 956 on the structure that houses the actuators 970, e.g. as part of the controller box. The actuators may project "pins" 960 which can mate with the dimpled connectors and convey force from the actuators to the tendons. Thus, for example, an actuator may cause a pin 960 to apply pressure to a corresponding dimpled receiver 962. The dimpled receiver translates the pushing of the pin into a tensile or compressive force applied to the affiliated tendon. This could be achieved using levers to reverse the direction of the force, for example. Since every pin preferably mates to a corresponding receiver, it is desirable to maintain the register of the connectors from the endoscope and the actuators. An orientation notch 954 on the connector that fits into a receiving orientation mate 958 on the actuator could be used to align both interfaces. Alternatively, the arrangement of the pins and receptacles could be orientation specific.

This feature is not limited to pins and receptacles, since virtually any convenient mechanism for transferring force from the actuator to the tendons would work. FIG. 11B shows a second variation of a quick-release mechanism for attaching and detaching the tendon driven endoscope from the actuators that relies on a nail-head configuration to actuate the tendons. The tendons preferably terminate in a flattened out protrusion resembling a nail-head 972. The array of nail-heads project from the connector interface 952 at the end of the umbilicus holding the endoscope tendons 950, and can mate with slotted holes 974 on the interface 956 of the actuator mechanism 970. Thus the slotted holes 974 of the actuators can be individually retracted by the actuators to apply tension to individual tendons. The quick-release mechanism could also be designed allow users to use different tendon driven endoscopes, even of different configurations, from the same actuator and/or controller unit.

Figure 12A:
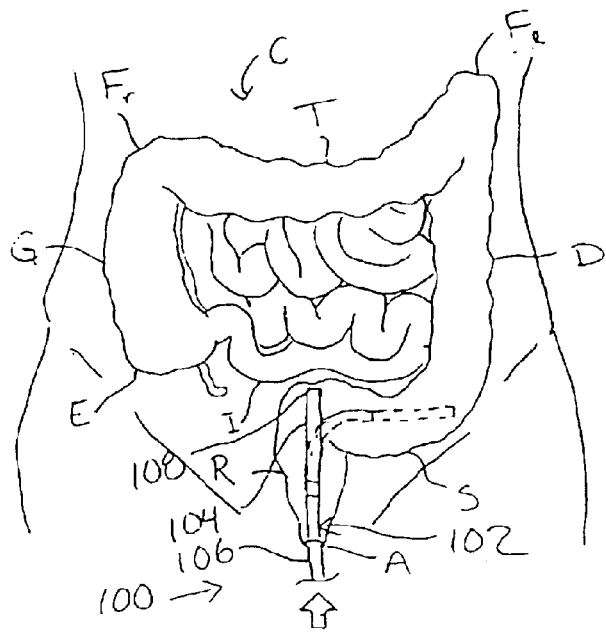
FIGS. 12A to 12E illustrate a representative example of advancing an endoscope through a patient's colon using a tendon driven endoscope of the present invention.

FIGS. 12A to 12F show the endoscope 100 of the present invention being employed for a colonoscopic examination of a patient's colon. In FIG. 12A, the endoscope body 102 has been lubricated and inserted into the patient's colon C through the anus A. The distal end 108 of the endoscope body 102 is advanced through the rectum R until the first turn in the colon C is reached, as observed through the ocular or on a video monitor. To negotiate the turn, the selectively steerable distal portion 104 of the endoscope body 102 is manually steered toward the sigmoid colon S by the user through the steering control. The control signals from the steering control to the selectively steerable distal portion 104 are monitored by the electronic motion controller 49. When the correct curve of the selectively steerable distal portion 104 for advancing the distal end 108 of the endoscope body 102 into the sigmoid colon S has been selected, the curve is logged into the memory of the controller 45 as a reference. This step can be performed in a manual mode, in which the user gives a command to the controller 45 to record the selected curve, using keyboard commands or voice commands. Alternatively, this step can be performed in an automatic mode, in which the user signals to the controller that the desired curve has been selected by advancing the endoscope body 102 distally. In this way, a three dimensional map of the colon or path may be generated and maintained for future applications.

In one variation, the curve is entered into the controller's memory by recording the change in lengths of the sides of the steerable distal portion after the distal portion has been articulated into the selected shape. In variations where the tendons are Bowden-type cables, the change in the length of the distal portion may be determined from the distance traveled by the tendon cable after steering the distal portion from the neutral, unbent, position. This distance traveled by the tendon cable may be determined relative to the cable housing or to another point located within the controller. Likewise, the change in lengths of the sides of any controllable segment can be determined in the same way.

As the endoscope is advanced distally, a curve is propagated proximally down the endoscope by setting the lengths of the sides of the more proximal segment equal to the lengths of the same sides of the steerable distal tip when the distal tip was in approximately the same axial position. In one variation the lengths of the sides are equal to the lengths of the non-extensible, non-compressible tendons. The tendons in the more proximal segment are tensioned or compressed so that the sides of the proximal segment are approximately equal in length to the recorded lengths of the sides of the distal region when it was in the same position. Alternatively, if the controllable segments are of different lengths from each other and/or the steerable distal tip, ratios of the lengths of the sides of the steerable distal tip can be used to propagate the selected curve down the endoscope rather than absolute lengths. In variations where the endoscope is withdrawn, or moved proximally, the lengths of tendons controlling more proximal segments can be used to set the lengths of the tendons controlling more distal segments.

Whether operated in manual mode or automatic mode, once the desired curve has been selected with the selectively steerable distal portion 104, the endoscope body 102 is advanced distally. The axial motion is detected by the axial motion transducer, or datum, and the selected curve is propagated proximally along the automatically controlled proximal portion 106 of the endoscope body 102 by the controller 45, as described above. The curve remains fixed in space while the endoscope body 102 is advanced distally through the sigmoid colon S. In a particularly tortuous colon, the selectively steerable distal portion 104 may have to be steered through multiple curves to traverse the sigmoid colon S.

Figure 12B:
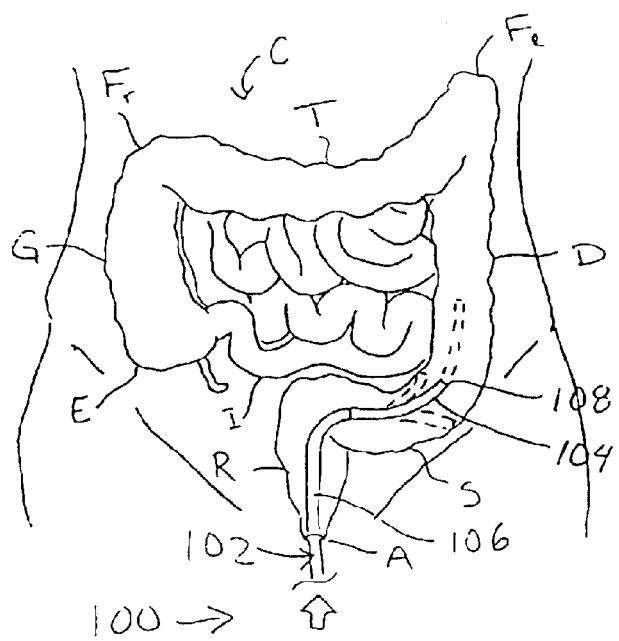
Figure 12C:
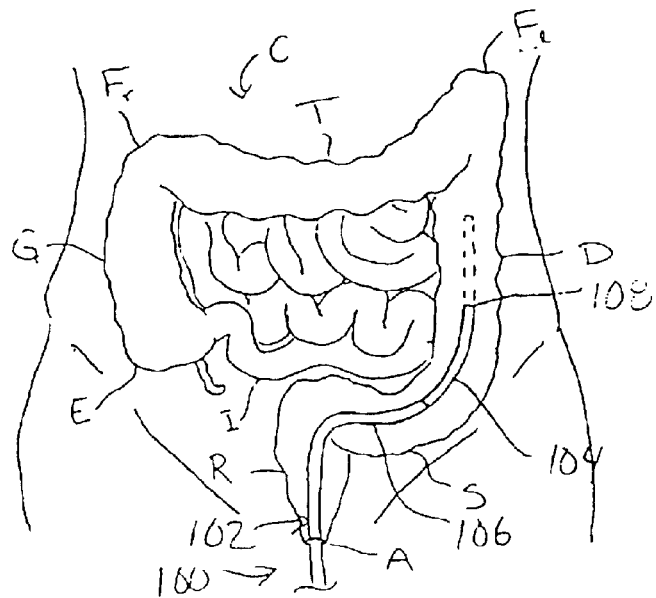

As illustrated in FIG. 12B, the user may stop the endoscope 100 at any point for examination or treatment of the mucosal surface or any other features within the colon C. The selectively steerable distal portion 104 may be steered in any direction to examine the inside of the colon C. When the user has completed the examination of the sigmoid colon S, the selectively steerable distal portion 104 is steered in a superior direction toward the descending colon D. Once the desired curve has been selected with the selectively steerable distal portion 104, the endoscope body 102 is advanced distally into the descending colon D, and the second curve as well as the first curve are propagated proximally along the automatically controlled proximal portion 106 of the endoscope body 102, as shown in FIG. 12C.

If, at any time, the user decides that the path taken by the endoscope body 102 needs to be revised or corrected, the endoscope 100 may be withdrawn proximally and the controller 45 commanded to erase the previously selected curve. This can be done manually using keyboard commands or voice commands or automatically by programming the controller 45 to go into a revise mode when the endoscope body 102 is withdrawn a certain distance. The revised or corrected curve is selected using the selectively steerable distal portion 104, and the endoscope body 102 is advanced as described before. Alternatively, the user can select a "relaxed" or "reset" mode from the motion controller, allowing the automatically controllable proximal portion of the endoscope, possibly including the steerable distal tip, to be passively advanced or withdrawn.

Figure 12D:
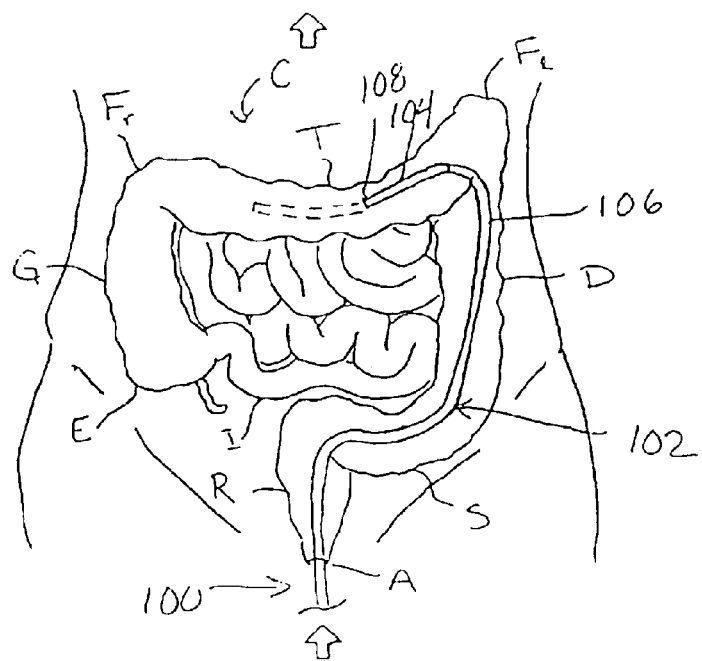
Figure 12E:
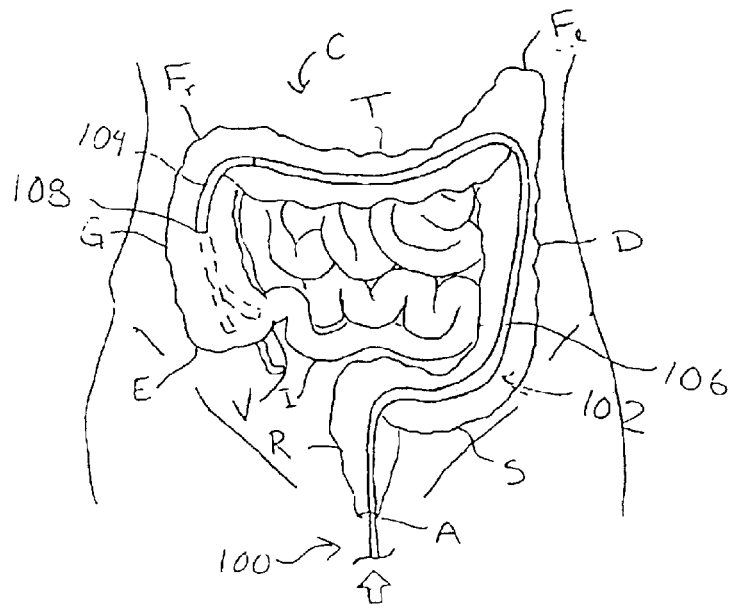

The endoscope body 102 is advanced through the descending colon D until it reaches the left (splenic) flexure $F_l$ of the colon. Here, in many cases, the endoscope body 102 must negotiate an almost 180 degree hairpin turn. As before, the desired curve is selected using the selectively steerable distal portion 104, and the endoscope body 102 is advanced distally through the transverse colon T, as shown in FIG. 12D. Each of the previously selected curves is propagated proximally along the automatically controlled proximal portion 106 of the endoscope body 102. The same procedure is followed at the right (hepatic) flexure $F_r$ of the colon and the distal end 108 of the endoscope body 102 is advanced through the ascending colon G to the cecum E, as shown in FIG. 12E. The cecum E, the ileocecal valve V and the terminal portion of the ileum I can be examined from this point using the selectively steerable distal portion 104 of the endoscope body 102.

Figure 12F:
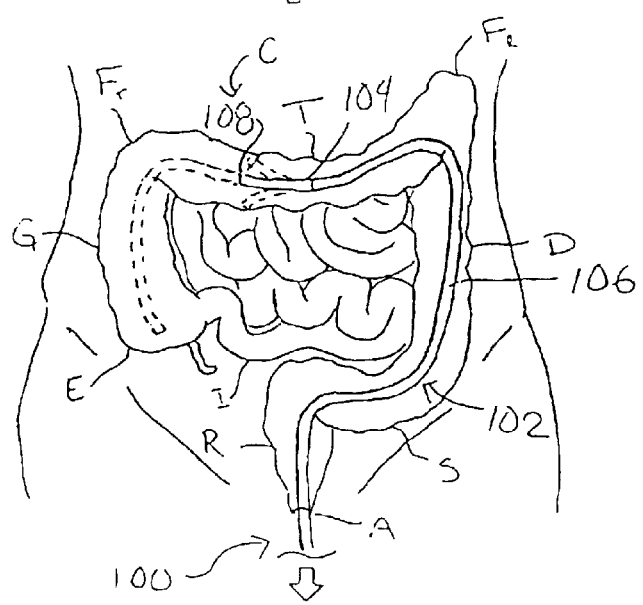
FIG. 12F illustrates a variation on withdrawing the tendon driven endoscope of the present invention.

FIG. 12F shows the endoscope 100 being withdrawn through the colon C. As the endoscope 100 is withdrawn, the endoscope body 102 follows the previously selected curves by propagating the curves distally along the automatically controlled proximal portion 106, as described above. At any point, the user may stop the endoscope 100 for examination or treatment of the mucosal surface or any other features within the colon C using the selectively steerable distal portion 104 of the endoscope body 102. At any given time, the endoscope 100 may be withdrawn or back-driven by a desired distance.

Thus, when the endoscope 100 is withdrawn proximally, each time it is moved proximally, the automatically controlled proximal portion 106 is signaled to assume the shape that previously occupied the space that it is now in. The curve propagates distally along the length of the automatically controlled proximal portion 106 of the endoscope body 102, and the shaped curve appears to be fixed in space as the endoscope body 102 withdraws proximally. Alternatively, the segments of controlled portion 28 could be made to become flaccid and the withdrawal would then be passive.

To initialize or calibrate the endoscope 100, the entire system may be calibrated prior to use and even during use. During endoscope procedures, such as those described above, various errors may accumulate in the controller and/or computer. These errors may arise from a variety of factors, e.g., errors in detecting cable motion, software errors in the controller and/or computer, positioning inaccuracies, etc.

To account for such possible errors, the position of endoscope 100 at any arbitrary position and/or depth of insertion relative to a fixed reference point, as described above, may be utilized as an additional reference for executing the advancement and withdrawal by re-initializing the endoscope 100 and the system while endoscope 100 is in use within the body of the patient. This newly-created additional reference point may be used for advancing the endoscope 100 further past this new reference. In this case, selectably steerable distal portion 104 may be used to define new, advancing conditions, as described above.

In the case of withdrawing endoscope 100 relative to the re-initialized reference point, the distal portion 104 can remain under the surgeon's control. Proximal portion 106 are placed under the control of the computer and are made to conform to the positions of the more-proximal segments at each depth of insertion as endoscope 100 is withdrawn similarly to the method described above.

Initialization or re-initialization may be performed manually if so desired. To accomplish this, once the surgeon or technician detects excessive error accumulation in the operation of endoscope 100, or if the computer detects an error level beyond a predetermined level, the controller may be programmed to re-initialize periodically, e.g., every several seconds, several minutes, or three minutes, etc., based upon the degree of error accumulation. Alternatively, this re-initializing process may be performed at least once during an exploratory or treatment procedure or it may be performed an arbitrary number of times, again depending upon the error accumulation.

The controller may be configured to continuously compare the optimal position of each or several segments against achievable segment position and actuation effort. When detected discrepancies are larger than a predetermined value, a reinitialization may be performed.

Figure 13:
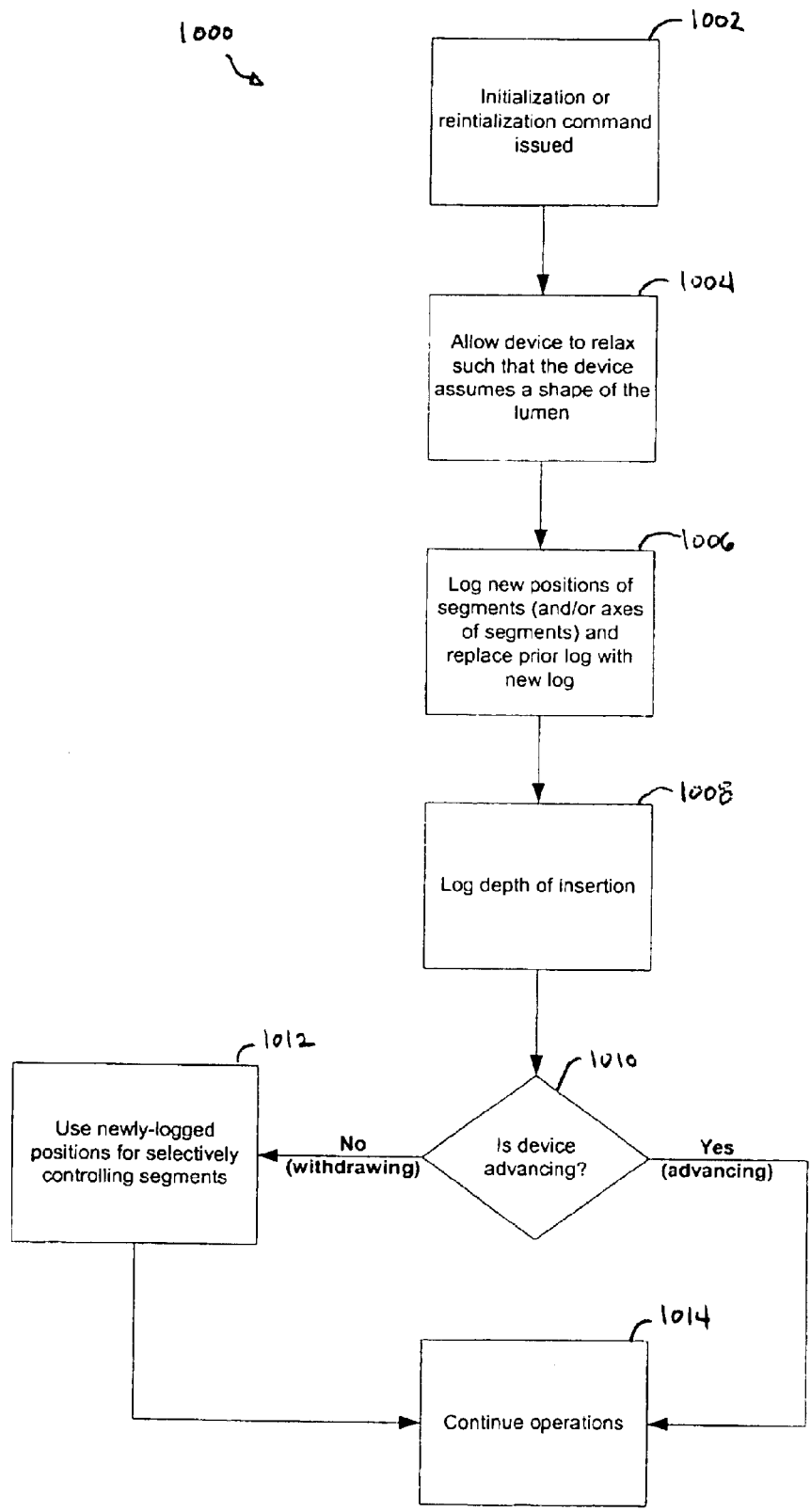
FIG. 13 shows a flow diagram for initializing or re-initializing an endoscopic device during a procedure.

FIG. 13 shows a flow diagram 1000 of one variation for initializing or re-initializing an endoscope device 100 during use in, e.g., a patient. Once it has been determined to initialize, e.g., prior to use, or re-initialize the device and system, an initialization or re-initialization command may be issued, as in step 1002. The endoscopic device may then be allowed to relax, i.e., no force is applied to the tendons to actuate movement of the segments, and assume a shape of the lumen or passageway in which the device is positioned, as in step 1004.

After the device has assumed the new positions, the new position information of the segments (and/or axes of the segments) may be logged into the computer to replace and/or supplement prior logged information with this newly logged information, as shown in step 1006. The depth of insertion may also be newly logged, as in step 1008.

Following logging the new positional information, it may be determined in step 1010 whether the endoscope 100 is advancing or withdrawing by sensing the motion, as described above. If the endoscope 100 is advanced, normal operations may continue as in step 1014 utilizing the newly logged information. If endoscope 100 is withdrawn, as in step 1012, the newly logged information may be used to control segments proximally located from the re-initialization reference point and normal operations may be continued, as in step 1014.

Although the endoscope of the present invention has been described for use as a colonoscope, the endoscope can be configured for a number of other medical and industrial applications. In addition, the present invention can also be configured as a catheter, cannula, surgical instrument or introducer sheath that uses the principles of the invention for navigating through tortuous body channels. The present invention may also be used for industrial applications such as inspection and exploratory applications within tortuous regions, e.g., machinery, pipes, etc.

In a variation of the method that is particularly applicable to laparoscopy or thoracoscopy procedures, the steerable endoscope can be selectively maneuvered along a desired path around and between organs in a patient's body cavity. The distal end of the endoscope may be inserted into the patient's body cavity through a natural opening, through a surgical incision or through a surgical cannula, introducer, or trocar. The selectively steerable distal portion can be used to explore and examine the patient's body cavity and to select a path around and between the patient's organs. The motion controller can be used to control the automatically controlled proximal portion to follow the selected path and, if necessary, to return to a desired location using the three-dimensional model in the electronic memory of the motion controller. Modification of the above-described assemblies and methods for carrying out the invention, and variations of aspects of the invention that are obvious to those of skill in the art are intended to be within the scope of the claims.

We claim:

1. An apparatus for insertion into a body cavity comprising: an elongated body comprising a plurality of articulatable segments and a steerable distal portion; a plurality of tensioning members attached to each of at least a majority of said segments;

each of said segments being configurable to assume a selected shape along an arbitrary path by actuation of the tensioning members attached thereto, wherein each of said segments is articulatable by at least one of said tensioning members;

said tensioning members extending from said segments to the proximal end of said elongated body and being configured to be coupled to an external control unit; and wherein said segments adjacent to one another are adapted to assume a selected shape of the adjacent segment by actuation of said tensioning members when the elongated body is advanced distally or proximally.

2. The apparatus of claim 1 further comprising a handle located proximal to said articulatable segments.

3. The apparatus of claim 2 further wherein paid steerable distal portion is configurable via controls located on said handle.

4. The apparatus of claim 1 wherein the steerable distal portion is configurable via said external control unit.

5. The apparatus of claim 1 wherein said control unit further comprises a computer.

6. The apparatus of claim 1 wherein said control unit is adapted to adjust said tensioning members for compressive and tensile forces applied to said tensioning members.

7. The apparatus claim 1 wherein said control unit further comprises actuators for applying force to articulate said tensioning members.

8. The apparatus of claim 7 wherein said actuators are selected from the group consisting of electromechanical motors, pneumatic and hydraulic cylinders, pneumatic and hydraulic motors, solenoids, shape memory alloy wires, and electronic rotary actuators.

9. The apparatus of claim 1 wherein said tensioning members are coupled to said external control unit via a quick-release attachment.

10. The apparatus of claim 1 wherein each of said segments are actuated by at least two of said tensioning members.

11. The apparatus of claim 10 further comprising at least one biasing element adapted to provide a biasing force in opposition to said tensioning members.

12. The apparatus of claim 1 wherein a segment proximal to another segment is adapted to assume the selected shape of the segment more distally located by actuation of said tensioning members when the apparatus is advanced distally.

13. The apparatus of claim 1 wherein a segment distal to another segment is adapted to assume the selected shape of the segment more proximally located by actuation of said tensioning members when the apparatus is retracted proximally.

14. The apparatus of claim 1 wherein the proximal segments are longer relative to a length of the distal segments.

15. The apparatus of claim 1 wherein the proximal segments have a wider diameter relative to a diameter of the distal segments.

16. The apparatus of claim 1 further comprising a flexible, passive tubular member extending proximally from said elongated and segmented body.

17. The apparatus of claim 1 wherein each of said segments comprise a plurality of control rings and said control rings have passages defined therethrough comprising a lumen.

18. The apparatus of claim 17 wherein said control rings further comprise hinges for attaching to adjacent control rings.

19. The apparatus of claim 17 wherein said elongated body further comprises a flexible backbone axially located within said elongated body to which said control rings are attachable.

20. The apparatus of claim 17 wherein each said tensioning members comprises a tendon cable and a tendon housing radially encompassing said tendon cable such that said tendon cable is free to move axially within said tendon housing.

21. The apparatus of claim 20 wherein the most distal control ring of each of said segments further comprises attachment sites for at least two of said tendon cables,
wherein the control rings proximal to the most distal control ring of each of said segments further comprise passageways for at least two of said tendon cables, and
wherein the most proximal control ring of each of said segments further comprises attachment sites for said tendon housings.

22. The apparatus of claim 1 wherein the elongated body defines one or more lumens therethrough.

23. A system for inserting an apparatus into a body cavity, comprising:
an elongate body having a proximal end and a selectively steerable distal end, the elongate body comprising a plurality of segment;
at least two tensioning members attached to each of at least a majority of segments for actuating said segments and wherein when the distal end assumes a selected curve, the selected curve is propagatable along the elongate body by said tensioning members selectively actuating said segments; and
a control unit in communication with each of the segments for selectively controlling each tensioning member to alter the relative position of the segments when the selected curve is propagated along the elongate body.

24. The system claim 23 further comprising an axial transducer having a sensor for measuring a distance the elongate body is advanced into or withdrawn from the body cavity.

25. The system of claim 23 further comprising a steering controller in communication with the steerable distal end for choosing the selected curve.

26. The system of claim 25 wherein the steering controller comprises a controller selected from the group consisting of joysticks, touch pads, track balls, mouse controllers, sensory gloves and control wheels.

27. The system of claim 26 further comprising an imaging system for transmitting an image from the distal end to the proximal end of the elongated body.

28. The system of claim 27 wherein the imaging system comprises a fiberoptic imaging bundle extending from the distal end to the proximal end of the elongate body.

29. The system claim 28 wherein the imaging system comprises a CCD camera.

30. The system of claim 28 wherein the imaging system comprises a CMOS camera.

31. The system of claim 23 further comprising at least one illumination source on the elongate body for providing a source of light.

32. The system of claim 31 wherein the illumination source comprises at least one illumination fiber extending from the distal end to the proximal end of the elongate body.

33. The system of claim 23 further comprising a recording device in communication with the elongate body for recording images from the distal end of the elongate body.

34. The system of claim 23 wherein the elongate body is configured as an endoscope for insertion into a patient's body.

35. The system of claim 23 wherein the elongate body is configured as a colonoscope for insertion into a patient's colon.

36. The system of claim 23 wherein the elongate body is configured as a laparoscope for insertion into a patient's body cavity.

37. The system of claim 23 wherein the elongated body defines one or more lumens therethrough.

38. A method of advancing an apparatus along a selected path, comprising:
providing an elongate body having a proximal end and a selectively steerable distal end, the elongate body comprising a plurality of segments and at least two tensioning members connected to each of at least a majority of segments for actuating said segments and wherein each tensioning members is independently controllable;

selectively steering the distal end to assume a first selected curve along a desired path; and advancing the elongate body distally while controlling the proximal end of the instrument to assume the first selected curve of the distal end.

39. The method of claim 38 further comprising measuring an axial position change of the elongate body while advancing the instrument distally.

40. The method of claim 39 further comprising incrementing a current axial position by the axial position change.

41. The method of claim 40 further comprising communicating to each segment to adjust a position of each segment while advancing the elongate body.

42. The method of claim 38 further comprising advancing the elongate body proximally while controlling the proximal end of the instrument to assume the first selected curve of the distal end.

43. The method of claim 42 further comprising measuring an axial position change of the elongate body while advancing the instrument proximally.

44. The method of claim 43 further comprising decrementing a current axial position by the axial position change.

45. The method of claim 44 further comprising communicating to each segment to adjust a position of each segment while advancing the elongate body.

46. The method of claim 38 further comprising re-initializing the apparatus such that the elongate body is recalibrated.

47. The method of claim 46 wherein re-initializing the apparatus comprises allowing the elongate body to conform to an arbitrary configuration.

48. The method of claim 47 further comprising storing at least one new position of at least one segment.

* * * * *